United States Patent
Torssell et al.

(10) Patent No.: US 12,344,590 B2
(45) Date of Patent: Jul. 1, 2025

(54) PROCESS FOR THE RECOVERY OF SOLVENT AND ISOLATION OF HUMIN MATERIALS AND COMPOSITIONS THEREOF

(71) Applicant: Stora Enso Oyj, Helsinki (FI)

(72) Inventors: Staffan Torssell, Bromma (SE); Marco Antonio Saucedo, Cambridge (GB); Christopher Paul Dunckley, San Jose, CA (US); Kenneth P. Keckler, Naperville, IL (US)

(73) Assignee: Stora Enso Oyj, Helsinki (FI)

( * ) Notice: Subject to any disclaimer, the term of this patent is extended or adjusted under 35 U.S.C. 154(b) by 886 days.

(21) Appl. No.: 17/594,328

(22) PCT Filed: Apr. 1, 2020

(86) PCT No.: PCT/US2020/026203
§ 371 (c)(1),
(2) Date: Oct. 11, 2021

(87) PCT Pub. No.: WO2020/214419
PCT Pub. Date: Oct. 22, 2020

(65) Prior Publication Data
US 2022/0162178 A1    May 26, 2022

Related U.S. Application Data

(60) Provisional application No. 62/834,143, filed on Apr. 15, 2019.

(51) Int. Cl.
*C07D 307/46*    (2006.01)

(52) U.S. Cl.
CPC .................. *C07D 307/46* (2013.01)

(58) Field of Classification Search
None
See application file for complete search history.

(56) References Cited

U.S. PATENT DOCUMENTS

| | | |
|---|---|---|
| 9,181,210 B2 | 11/2015 | Hutchenson et al. |
| 9,206,149 B2 | 12/2015 | Janka et al. |
| 9,504,994 B2 | 11/2016 | Janka et al. |

(Continued)

FOREIGN PATENT DOCUMENTS

| | | |
|---|---|---|
| CN | 107848995 A | 3/2018 |
| CN | 109195958 A | 1/2019 |

(Continued)

OTHER PUBLICATIONS

Chinese Office Action dated Mar. 25, 2023 for Application No. 202080036474.5; 10 pages.

(Continued)

*Primary Examiner* — Michael Forrest
*Assistant Examiner* — Nicole Lee Quist
(74) *Attorney, Agent, or Firm* — Knobbe, Martens, Olson & Bear, LLP (57) ABSTRACT

Novel processes for recovering solvents and isolating humin or humate materials from 5-hydroxymethylfurfural (HMF) and 2,5-furandicarboxylic acid (FDCA) pathway processes are described. In some embodiments, the process utilizes a thin film evaporator, such as a horizontal thin film evaporator (HTFE).

9 Claims, 2 Drawing Sheets

(56) References Cited

U.S. PATENT DOCUMENTS

| | | | |
|---|---|---|---|
| 10,010,812 B2 | 7/2018 | Parker et al. | |
| 2013/0252302 A1 | 9/2013 | Pan et al. | |
| 2013/0345450 A1 | 12/2013 | Böhling et al. | |
| 2014/0371473 A1* | 12/2014 | Blank | C07D 307/46 422/187 |
| 2017/0158656 A1 | 6/2017 | Boussie et al. | |
| 2017/0197930 A1 | 7/2017 | Sokolovskii et al. | |
| 2018/0093894 A1 | 4/2018 | Smith et al. | |
| 2018/0093961 A1 | 4/2018 | Howard et al. | |
| 2020/0148656 A1 | 5/2020 | Divekar et al. | |

FOREIGN PATENT DOCUMENTS

| | | | |
|---|---|---|---|
| JP | 2008-239642 A | 10/2008 | |
| JP | 2010-027520 A | 2/2010 | |
| JP | 2011-153192 A | 8/2011 | |
| JP | 2017-505310 A | 2/2017 | |
| KR | 20140101848 A | 8/2014 | |
| WO | WO-2011124639 A1 * | 10/2011 | C07D 307/46 |
| WO | WO 2013/053816 A1 | 4/2013 | |
| WO | WO 2013/087614 A1 | 6/2013 | |
| WO | WO 2015/113060 | 7/2015 | |
| WO | WO 2015/113060 A2 | 7/2015 | |
| WO | WO 2016/076711 A1 | 5/2016 | |
| WO | WO-2016113678 A1 * | 7/2016 | C07D 307/50 |
| WO | WO 2017/019441 A1 | 2/2017 | |

OTHER PUBLICATIONS

India Examination Report dated Nov. 14, 2023 for Application No. 202117051075; 6 pages.

Walton et al., "Inhibition effects on fermentation of hardwood extracted hemicelluloses by acetic acid and sodium", Bioresource Technology, 2010, vol. 101, No. 6, pp. 1935-1940.

Notice of Reasons for Refusal for Japanese Patent Application No. JP 2021-561613 mailed on Jan. 30, 2024 by Japanese Patent Office.

Buss-SMS-Canzler. Evaporation Technology. https://www.sms-vt.com/hubfs/PDF/Downloads/Buss-SMS-Canzler_Evaporation_Technology.pdf.

Hyde, W. et al., Evaporation of difficult products-Agitated thin-film evaporation overcomes common problems, Chemical Processing, vol. 60, No. 2, pp. 59.

Patent Examination Report 1 for New Zealand Application No. 780809 dated Feb. 19, 2024.

Kröger et al., A new approach for the production of 2,5-furandicarboxylic acid by in situ oxidation of 5-hydroxymethylfurfural starting from fructose. Topics in Catalysis (2000) 13: 237-242.

Rasrendra et al., Experimental studies on the pyrolysis of humins from the acid-catalysed dehydration of C6-sugars. J Analyt Appl Pyrolysis (2013) 104: 299-307.

International Search Report in International Application No. PCT/US2020/026203 mailed on Jan. 7, 2020.

Motagamwala et al., Solvent system for effective near-term production of hydroxymethylfurfural (HMF) with potential for long-term process improvement. Ener Environ Science. Apr. 12, 2019;12(7): 2212-2222.

Agarwal et al., Catalytic pyrolysis of recalcitrant, insoluble humin byproducts from C6 sugar biorefineries. J Anal Appl Pyrolysis 2017;123: 134-143.

Hoang et al., Humin based by-products from biomass processing as a potential carbonaceous source for synthesis gas production. Green Chem. 2015;17(2): 959-972.

Van Zandvoort et al., Formation, molecular structure, and morphology of humins in biomassconversion: influence of feedstock and processing conditions. ChemSusChem. Sep. 2013;6(9): 1745-1758.

* cited by examiner

FIG. 1

FIG. 2

PROCESS FOR THE RECOVERY OF SOLVENT AND ISOLATION OF HUMIN MATERIALS AND COMPOSITIONS THEREOF

CROSS REFERENCE TO RELATED APPLICATIONS

This application is U.S. National Phase under 35 U.S.C. § 371 of International Application No. PCT/US2020/026203, filed Apr. 1, 2020, designating the U.S. and published in English as International Pub. No. WO 2020/214419, which claims the benefit of U.S. Provisional Application No. 62/834,143 filed Apr. 15, 2019, each of which is expressly incorporated by reference herein in its entirety for all purposes.

BACKGROUND

Field

The present disclosure relates to processes for recovering solvents and isolating humin or humate materials from 2,5-furandicarboxylic acid pathway products.

Description of the Related Art

Low cost and renewably-derived 2,5-furandicarboxylic acid (FDCA) and its derivatives harbor considerable potential for commercial applications. In certain applications, they have the potential to displace aromatic dicarboxylic acids such as terephthalic and isophthalic acid. Methods of producing FDCA from various feedstocks have been reported, but in such methods it is difficult to efficiently recover solvents and remove impurities and/or by-products from the feedstocks, such as humin or humate compounds. Accordingly, there remains a need for improved systems and approaches for solvent recovery and impurity removal in 5-hydroxymethylfurfural (HMF) and FDCA pathway processes.

SUMMARY

In one aspect, a process for isolating humins from a feed source is disclosed. The process includes providing a feed source to a thin-film evaporator. The feed source includes about 65-90 wt. % or 65-90 wt. % of a multicomponent solvent comprising water and a water-miscible aprotic organic solvent, and about 10-35 wt. % or 10-35 wt. % of a dissolved dry residue. The dissolved dry residue includes, in wt. % or ppm of the total feed source, a sugar content of about 30,000-120,000 ppm or 30,000-120,000 ppm, a furan containing compound content of about 2-5 wt. % or 2-5 wt. %, a humin compound content of about 24,000-100,000 ppm or 24,000-100,000 ppm, an organic acid content of about 0.2-0.7 wt % or 0.2-0.7 wt %, a homogenous acid, a salt, and a metal. The process further includes wherein the feed source has a pH of between about 1-4 pH or 1-4 pH and processing the feed source within the thin-film evaporator to provide an isolated solid material. The isolated solid material includes a moisture content of about 0.3-2 wt. % or 0.3-2 wt. %, a furan containing compound content of about 0.9-5 wt. % or 0.9-5 wt. %, a sugar content of about 0.1-2 wt. % or 0.1-2 wt. %, a dioxane content of about 0.02-1 wt. % or 0.02-1 wt. %, and an ash content of about 0.1-6 wt. % or 0.1-6 wt. %.

In some embodiments, the process further includes washing and drying the isolated solid material to produce a washed and dried solid material. In some embodiments, the process further includes exposing the washed and dried solid material to a high temperature carbonization process to produce a carbonized solid material. In some embodiments, the thin-film evaporator is a horizontal thin film evaporator. In some embodiments, the thin-film evaporator is orientated at an angle between or between about 0° to 90° such as at or about at 5°, 10°, 15°, 30°, 45°, 60°, 75°, 80°, 85°, or any range of values there between, wherein 0° corresponds to the heated thin film evaporator being oriented straight down, toward the Earth's center of mass and 180° corresponds to the heated thin film evaporator being oriented straight up, away from the Earth's center of mass.

In some embodiments, the organic acid is selected from the group consisting of levulinic acid, formic acid, acetic acid, and combinations thereof. In some embodiments, the homogenous acid is selected from the group consisting of HCl, HBr, HI, $H_2SO_4$, $H_3PO_4$, oxalic acid, triflic acid, methane sulfonic acid, boron trihalides, and combinations thereof. In some embodiments, the salt is selected from the group consisting of sodium bromide, calcium bromide, sodium chloride, calcium chloride, potassium chloride, potassium chloride, magnesium chloride, magnesium chloride, and combinations thereof.

In another aspect, a process for recovering solvent from a feed source is disclosed. The process includes providing a feed source to a thin-film evaporator. The feed source includes about 65-90 wt. % or 65-90 wt. % of a multicomponent solvent comprising water and a water-miscible aprotic organic solvent, and about 10-35 wt. % or 10-35 wt. % of a dissolved dry residue. The dissolved dry residue includes, in wt. % or ppm of the total feed source, a sugar content of about 30,000-120,000 ppm or 30,000-120,000 ppm, a furan containing compound content of about 2-5 wt. % or 2-5 wt. %, a humin compound content of about 24,000-100,000 ppm or 24,000-100,000 ppm, an organic acid content of about 0.2-0.7 wt % or 0.2-0.7 wt %, a homogenous acid, a salt, and a metal. The process further includes wherein the feed source has a pH of between about 1-4 pH or 1-4 pH, and processing the feed source within the thin-film evaporator to provide a recovered solvent material. The isolated solid material includes a sugar content of at most about 500 ppm or 500 ppm, a furan content of at most about 1.6 wt. % or 1.6 wt. %, a humin compound content of about 300-700 ppm or 300-700 ppm, and an organic acid content of at most about 2 wt. % or 2 wt. %.

In some embodiments, the process further includes providing the recovered solvent material to a condenser. In some embodiments, the process further includes providing the recovered solvent material to a continuous distillation column. In some embodiments, the recovered solvent is further purified or isolated by fractional distillation. In some embodiments, the thin-film evaporator is a horizontal thin film evaporator. In some embodiments, the thin-film evaporator is orientated at an angle between or between about 0° to 90° such as at or about at 5°, 10°, 15°, 30°, 45°, 60°, 75°, 80°, 85°, or any range of values there between, wherein 0° corresponds to the heated thin film evaporator being oriented straight down, toward the Earth's center of mass and 180° corresponds to the heated thin film evaporator being oriented straight up, away from the Earth's center of mass.

In another aspect, a composition of a solid material isolated from a feed source is disclosed. The composition includes a moisture content of less than 2 wt. %, a furan content of at least 0.9 wt. %, a sugar content of at least 0.1 wt. %, a moisture content of at most 2 wt. %, a dioxane content of at most 1 wt. %, and an ash content of at most 6 wt. %.

In some embodiments, the ash content is at most 1 wt. %. In some embodiments, the ash content is at most 0.5 wt. %. In some embodiments, the ash content is at most 0.1 wt. %.

In another aspect, a process for isolating humins from a feed source is provided. The process includes providing a feed source to a thin-film evaporator, wherein the feed source includes a multicomponent solvent comprising water and a water-miscible aprotic organic solvent, and a dissolved dry residue comprising a humin compound content, wherein the feed source has a pH of between about 1-4 pH or 1-4 pH, and processing the feed source within the thin-film evaporator to provide an isolated solid material includes a moisture content of about 0.3-2 wt. % or 0.3-2 wt. %, a furan containing compound content of about 0.9-5 wt. % or 0.9-5 wt. %, a sugar content of about 0.1-2 wt. % or 0.1-2 wt. %, a dioxane content of about 0.02-1 wt. % or 0.02-1 wt. %, and an ash content of about 0.1-6 wt. % or 0.1-6 wt. %.

In another aspect, a process for recovering solvent from a feed source is provided. The process includes providing a feed source to a thin-film evaporator, wherein the feed source includes a multicomponent solvent comprising water and a water-miscible aprotic organic solvent, and a dissolved dry residue comprising a humin compound content, wherein the feed source has a pH of between about 1-4 pH or 1-4 pH, and processing the feed source within the thin-film evaporator to provide a recovered solvent material including a sugar content of at most about 500 ppm or 500 ppm, a furan content of at most about 1.6 wt. % or 1.6 wt. %, a humin compound content of about 300-700 ppm or 300-700 ppm, and an organic acid content of at most about 2 wt. % or 2 wt. %.

Preferred alternatives include but are not limited to:

1. A process for isolating humins from a feed source, comprising:
   providing a feed source to a thin-film evaporator, wherein the feed source comprises:
     about 65-90 wt. % or 65-90 wt. % of a multicomponent solvent comprising water and a water-miscible aprotic organic solvent; and
     about 10-35 wt. % or 10-35 wt. % of a dissolved dry residue comprising, in wt. % or ppm of the total feed source:
       a sugar content of about 30,000-120,000 ppm or 30,000-120,000 ppm;
       a furan containing compound content of about 2-5 wt. % or 2-5 wt. %;
       a humin compound content of about 24,000-100,000 ppm or 24,000-100,000 ppm;
       an organic acid content of about 0.2-0.7 wt % or 0.2-0.7 wt %;
       a homogenous acid;
       a salt; and
       a metal;
     wherein the feed source has a pH of between about 1-4 pH or 1-4 pH; and
   processing the feed source within the thin-film evaporator to provide an isolated solid material comprising:
     a moisture content of about 0.3-2 wt. % or 0.3-2 wt. %;
     a furan containing compound content of about 0.9-5 wt. % or 0.9-5 wt. %;
     a sugar content of about 0.1-2 wt. % or 0.1-2 wt. %;
     a dioxane content of about 0.02-1 wt. % or 0.02-1 wt. %; and
     an ash content of about 0.1-6 wt. % or 0.1-6 wt. %.

2. The process of alternative 1, further comprising washing and drying the isolated solid material to produce a washed and dried solid material.

3. The process of alternative 2, further comprising exposing the washed and dried solid material to a high temperature carbonization process to produce a carbonized solid material.

4. The process of anyone of alternatives 1-3, wherein the thin-film evaporator is a horizontal thin film evaporator.

5. The process of any one of alternatives 1-4, wherein the thin-film evaporator is orientated at an angle between or between about 0° to 90° such as at or about at 5°, 10°, 15°, 30°, 45°, 60°, 75°, 80°, 85°, or any range of values there between, wherein 0° corresponds to the heated thin film evaporator being oriented straight down, toward the Earth's center of mass and 180° corresponds to the heated thin film evaporator being oriented straight up, away from the Earth's center of mass.

6. The process of any one of alternatives 1-5, wherein the organic acid is selected from the group consisting of levulinic acid, formic acid, acetic acid, and combinations thereof.

7. The process of any one of alternatives 1-6, wherein the homogenous acid is selected from the group consisting of HCl, HBr, HI, $H_2SO_4$, $H_3PO_4$, oxalic acid, triflic acid, methane sulfonic acid, boron trihalides, and combinations thereof.

8. The process of any one of alternatives 1-7, wherein the salt is selected from the group consisting of sodium bromide, calcium bromide, sodium chloride, calcium chloride, potassium chloride, potassium chloride, magnesium chloride, magnesium chloride, and combinations thereof.

9. A process for recovering solvent from a feed source, comprising:
   providing a feed source to a thin-film evaporator, wherein the feed source comprises:
     about 65-90 wt. % or 65-90 wt. % of a multicomponent solvent comprising water and a water-miscible aprotic organic solvent; and
     about 10-35 wt. % or 10-35 wt. % of a dissolved dry residue comprising, in wt. % or ppm of the total feed source:
       a sugar content of about 30,000-120,000 ppm or 30,000-120,000 ppm;
       a furan containing compound content of about 2-5 wt. % or 2-5 wt. %;
       a humin compound content of about 24,000-100,000 ppm or 24,000-100,000 ppm;
       an organic acid content of about 0.2-0.7 wt % or 0.2-0.7 wt %;
       a homogenous acid;
       a salt; and
       a metal;
     wherein the feed source has a pH of between about 1-4 pH or 1-4 pH; and
   processing the feed source within the thin-film evaporator to provide a recovered solvent material comprising:
     a sugar content of at most about 500 ppm or 500 ppm;
     a furan content of at most about 1.6 wt. % or 1.6 wt. %;

a humin compound content of about 300-700 ppm or 300-700 ppm; and an organic acid content of at most about 2 wt. % or 2 wt. %.

10. The process of alternative 9, further comprising providing the recovered solvent material to a condenser.

11. The process of alternative 9, further comprising providing the recovered solvent material to a continuous distillation column.

12. The process of alternative 9, wherein the recovered solvent is further purified or isolated by fractional distillation.

13. The process of any one of alternatives 9-12, wherein the thin-film evaporator is a horizontal thin film evaporator.

14. The process of any one of alternatives 9-13, wherein the thin-film evaporator is orientated at an angle between or between about 0° to 90° such as at or about at 5°, 10°, 15°, 30°, 45°, 60°, 75°, 80°, 85°, or any range of values there between, wherein 0° corresponds to the heated thin film evaporator being oriented straight down, toward the Earth's center of mass and 180° corresponds to the heated thin film evaporator being oriented straight up, away from the Earth's center of mass.

15. A composition of a solid material isolated from a feed source, comprising:
a moisture content of less than 2 wt. %;
a furan content of at least 0.9 wt. %;
a sugar content of at least 0.1 wt. %;
a moisture content of at most 2 wt. %;
a dioxane content of at most 1 wt. %;
an ash content of at most 6 wt. %.

16. The composition of alternative 15, wherein the ash content is at most 1 wt. %.

17. The composition of alternative 15, wherein the ash content is at most 0.5 wt. %.

18. The composition of alternative 15, wherein the ash content is at most 0.1 wt. %.

19. A process for isolating humins from a feed source, comprising:
providing a feed source to a thin-film evaporator, wherein the feed source comprises:
a multicomponent solvent comprising water and a water-miscible aprotic organic solvent; and
a dissolved dry residue comprising a humin compound content;
wherein the feed source has a pH of between about 1-4 pH or 1-4 pH; and
processing the feed source within the thin-film evaporator to provide an isolated solid material comprising:
a moisture content of about 0.3-2 wt. % or 0.3-2 wt. %;
a furan containing compound content of about 0.9-5 wt. % or 0.9-5 wt. %;
a sugar content of about 0.1-2 wt. % or 0.1-2 wt. %;
a dioxane content of about 0.02-1 wt. % or 0.02-1 wt. %; and
an ash content of about 0.1-6 wt. % or 0.1-6 wt. %.

20. A process for recovering solvent from a feed source, comprising:
providing a feed source to a thin-film evaporator, wherein the feed source comprises:
a multicomponent solvent comprising water and a water-miscible aprotic organic solvent; and
a dissolved dry residue comprising a humin compound content;
wherein the feed source has a pH of between about 1-4 pH or 1-4 pH; and
processing the feed source within the thin-film evaporator to provide a recovered solvent material comprising:
a sugar content of at most about 500 ppm or 500 ppm;
a furan content of at most about 1.6 wt. % or 1.6 wt. %;
a humin compound content of about 300-700 ppm or 300-700 ppm; and
an organic acid content of at most about 2 wt. % or 2 wt. %.

DETAILED DESCRIPTION

The present disclosure relates to several approaches to recover solvent and isolate humins or humates in 5-hydroxymethylfurfural (HMF) and/or furandicarboxylic acid (FDCA) product pathway processes. Exemplary methods for producing HMF and FDCA pathway products are disclosed in U.S. Patent Pub. No. 2017/0197930 and U.S. Patent Pub. No. 2017/0158656, which are hereby expressly incorporated by reference in their entireties for all purposes. In some FDCA product processes, for example a process whereby 5-hydroxymethylfurfural (HMF) is produced by dehydration of a sugar feedstock, humin or humate by-products are generated. It is to be understood that the terms humin(s) and humate(s) are interchangeable. Humins are polymerized sugars, polymerized dehydrated sugars, polymerized furanic compounds and/or other similar condensation reaction by-products generated in sugar dehydration or HMF pathway processes. Because humins are condensation products, they build up molecular weight through the condensation reactions. The condensation reactions can take place with multiple reaction species, and consequently multiple structurally distinct species can be formed that can have a wide distribution of molecular weights. The exact structures and distributions of humins material will depend on the dehydration conditions, for example, such as fructose concentration, the acid, the acid concentration, the solvent, the reaction temperature and the reaction time. As the molecular weights of the humins structures build up, their solubility limit may be exceeded causing humins to precipitate from the reaction solution causing operational difficulties, particularly in a retentate solution of a solvent recovery system. Furthermore, isolation and transportation of humins from a solvent recovery system is typically problematic because humins are isolated in the form of thick and viscous liquid that cools as a solid when isolated by traditional methods. Such viscous liquids that cool to solid materials are impediments to industrial processing applications. For example, although others have taught the isolation of solid furanic resins, such as U.S. Patent Pub. No. 2018/0093894, these traditionally isolated furanic resins are unlikely to be further processed in an industrially viable process.

The present disclosure describes several methods for isolating humin species from a membrane retentate solution by using a thin film evaporator. The thin film evaporator facilitates isolation of humins as a convenient free-flowing powder, wherein the free-flowing humins may be further processed to have beneficial downstream commercial applications. Obtaining a free-flowing powder conveniently allows for high throughput industrial processing applications. Additionally, the present evaporation method allows for >99% recovery of the solvent composition, which then becomes useful for recycling procedures. The present disclosure therefore provides cost effective approaches to separate and remove humins as a free-flowing powder and recover the reaction solvent composition for recycling back into the HMF and/or FDCA pathway processes.

HMF Pathway Process

In some embodiments, humins may be isolated from the retentate stream of an HMF pathway process. In some embodiments, the HMF pathway process comprises a sugar dehydration process. For example, any variety of carbohydrate feedstocks or fructose-containing feedstocks may be employed in the dehydration process. It is to be understood that the terms carbohydrate feedstocks or fructose-containing feedstocks may be used interchangeably.

In some embodiments, the dehydration or conversion of a fructose-containing feedstock to HMF is carried out by contacting a carbohydrate feedstock comprising a sugar and a dehydration solvent with a catalyst under conditions sufficient to form a (dehydration) reaction mixture for dehydrating the sugar to produce the furanic oxidation substrate (referred to herein as the "dehydration process"). In some embodiments, the sugar is a hexose, such as, for example, glucose, galactose, mannose, idose, a ketohexose, fructose, levulose, sorbose, tagatose, or allose, and the like, or starches, cellulosics and other forms of carbohydrates that may be subjected to processing conditions that isomerize glucose produced from the starches or cellulosics. In some embodiments, the sugar is glucose or fructose. In some embodiments, the sugar is fructose.

The term "dehydration solvent" refers to a solvent in which both the sugar and the furanic oxidation substrate are each separately soluble at a minimum level of at least 2% by weight at the temperature at which the dehydration reaction is carried out. Typically, the dehydration solvent is one in which the furanic oxidation substrate has a solubility of at least 3 wt %, at least 4 wt %, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, at least 15 wt %, at least 17%, at least 19%, at least 21%, at least 23%, or at least 25% as measured at the temperature at which the dehydration reaction is carried out. In some embodiments, the concentration of furanic oxidation substrate in the dehydration solvent ranges from or any number in between 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, 13-15 wt %, 14-16 wt %, 15-17 wt %, 16-18 wt %, 17-19 wt %, 18-20 wt %, 19-21 wt %, 20-22 wt %, 21-23 wt %, 22-24 wt %, or 23-25 wt % or within a range defined by any of two of the aforementioned weight percentages. Typically, the dehydration solvent comprises water and/or a water-miscible organic solvent. More typically, the dehydration solvent is a multi-component solvent. Usually, the multi-component solvent employed in the dehydration process comprises water and a water-miscible aprotic organic solvent. Water-miscible aprotic organic solvents and multi-component solvent compositions that are suitable for use in the dehydration process are the same as those that are suitable for use in the FDCA pathway product-generating processes as described hereinabove. In some embodiments, the water-miscible aprotic organic solvent is N-Methyl-2-Pyrrolidone (NMP). In some embodiments, the carbohydrate feedstock comprises fructose and the furanic oxidation substrate comprises HMF.

Exemplary water-miscible aprotic solvents suitable for use in a dehydration solvent comprise tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), or gamma-valerolactone, or any mixture thereof. Preferably, the water-miscible aprotic organic solvent is an ether, such as, for example, a glyme, dioxane (1,4-dioxane), a dioxolane (e.g., 1,3-dioxolane), or tetrahydrofuran, or any mixture thereof. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, or a highly ethoxylated diether of a high molecular weight alcohol ("higlyme"), or any mixture thereof. Often, the dehydration solvent is a multi-component solvent comprising water and a water-miscible aprotic organic solvent that is glyme, diglyme, or dioxane.

In some embodiments, the water-miscible organic solvent species is at least 5 volume % (vol %), at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component system.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

In some embodiments, the volume ratio of water to water-miscible organic solvent is in the range from or any number in between 1:6 to 6:1. In certain embodiments, the volume ratio is from or any number in between 1:4 to 4:1 water:water-miscible organic solvent. In other embodiments, the volume ratio is from or any number in between 1:4 to 3:1 water:water miscible organic solvent. In other embodiments, the volume ratio is from or any number in between 1:3 to 3:1 water:water miscible organic solvent. In certain embodiments, the volume ratio is 1:1 water:water-miscible organic solvent.

In some embodiments, the multi-component solvent comprises water and two different water-miscible organic solvents. Typically, both of the water-miscible organic solvents are water-miscible aprotic organic solvents. Each of the two water-miscible aprotic solvents can be independently selected from the group of tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), or gamma-valerolactone. One or both of the water-miscible aprotic organic solvent can be an ether, such as, for example, a glyme, dioxane (for example 1,4-dioxane), dioxolane (e.g., 1,3-dioxolane), or tetrahydrofuran, and the like. Glymes include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, or a highly ethoxylated diether of a high molecular weight alcohol ("higlyme"), and the like.

In some embodiments, the volume ratio of water to the first and second water-miscible organic solvent is approximately 1:1:1 (v:v:v). In some embodiments, the volume ratio of water to the first and second water-miscible organic solvent is approximately 1:2:1 (v:v:v). In some embodiments, the volume ratio of water to the first and second water-miscible organic solvent is approximately 1:2:2 (v:v:v). In some embodiments, the volume ratio of water to the first and second water-miscible organic solvent is approximately 2:1:1 (v:v:v).

The concentration of sugar in the carbohydrate feedstock is typically in the range of from or any number in between 2 wt % to 80 wt % or from or any number in between 5 wt % to 80 wt %. In various embodiments, the concentration of sugar is in the range of from or any number in between 20 wt % to 80 wt %. In some embodiments, the concentration of sugar in the carbohydrate feedstock is in the range of from or any number in between 5 wt % to 20 wt %. In other embodiments, the concentration of sugar in the carbohydrate feedstock is in the range of from or any number in between 5 wt % to 40 wt %. In some embodiments, the concentration of sugar in the carbohydrate feedstock ranges from or any number in between 5-15 wt %, 10-20 wt %, 15-25 wt %, 20-30 wt %, 25-35 wt %, 30-40 wt %, 35-45 wt %, 40-50 wt %, 45-55 wt %, 50-60 wt %, 55-65 wt %, 60-70 wt %, 65-75 wt % or 70-80 wt %, or within a range defined by any two of the aforementioned weight percentages.

In some embodiments, an aqueous solution of fructose is used as the feedstock to the reaction zone. In some embodiments, commercially available high fructose syrup (HFS) is dissolved in water to form the solution. For example, HFS-97 or HFS-90 may be used.

Catalysts that are suitable for use in the dehydration process include homogeneous catalysts, including, for example, homogeneous acid catalysts, and the like, as well as heterogeneous catalysts. In some embodiments, an acid catalyst is an acid selected from the group consisting of HBr, $H_2SO_4$, $HNO_3$, HCl, HI, $H_3PO_4$, triflic acid, methansulfonic acid, benzenesulfonic acid, and p-toluene sulfonic acid. In some embodiments, the acid catalyst is HCl. In some embodiments, the acid catalyst is HCl and does not further comprise a bromide salt. In some embodiments, the acid catalyst is HCl and the dehydration solvent does not comprises N-methyl-pyrrolidone (NMP).

In some embodiments, the acid catalyst is HBr. In some embodiments, when the acid catalyst is not HBr, the dehydration reaction mixture further comprises a bromide salt. In some embodiments, when the acid catalyst is not HBr, the dehydration reaction mixture further comprises a bromide salt and the dehydration solvent comprises N-methyl-pyrrolidone (NMP). In some embodiments, the acid catalyst can be selected from the group consisting of $H_2SO_4$, $HNO_3$, HCl, HI, $H_3PO_4$, triflic acid, methansulfonic acid, benzenesulfonic acid, and p-toluene sulfonic acid, and wherein the dehydration reaction mixture comprises a bromide salt. In some embodiments, the bromide salt can be selected from the group consisting of LiBr, NaBr, KBr, $MgBr_2$, $CaBr_2$, $ZnBr_2$, tetramethylammonium bromide, tetraethylammonium bromide, tetrapropylammonium bromide, and tetrabutylammonium bromide, or any combination of two or more thereof. The acid catalyst can further comprise a Lewis acid. The Lewis acid can be selected from the group consisting of a borontrihalide, an organoborane, an aluminum trihalide, a phosphorus pentafluoride, an antimony pentafluoride, a rare earth metal triflate, a metal halide, a metal trifluoroacetate, and a metal cation ether complex. The Lewis acid can be a metal halide. The metal halide can be $ZnCl_2$ or $ZnBr_2$.

Quantities of acid catalyst employed are typically in the range of from or any number in between 0.1 to 25 mol %, and more typically in the range of from or any number in between 0.5 to 5 mol % (wherein, mol % is calculated on the basis of moles of sugar, e.g., hexose). In some embodiments, the amount of acid catalyst in the reaction mixture for dehydrating the sugar results in the reaction mixture having an acidic pH. In some embodiments, the amount of acid catalyst in the reaction mixture for dehydrating the sugar results in the reaction mixture having a pH of less than 6. In some embodiments, the amount of acid catalyst in the reaction mixture for dehydrating the sugar results in the reaction mixture having a pH of less than 5. In some embodiments, the amount of acid catalyst in the reaction mixture for dehydrating the sugar results in the reaction mixture having a pH of less than 4. In some embodiments, the amount of acid catalyst in the reaction mixture for dehydrating the sugar results in the reaction mixture having a pH of less than 3. In some embodiments, the amount of acid catalyst in the reaction mixture for dehydrating the sugar results in the reaction mixture having a pH of less than 2. In some embodiments, the amount of acid catalyst in the reaction mixture for dehydrating the sugar results in the reaction mixture having a pH of less than 1.

The dehydration product solution may be used as a feedstock for producing an FDCA pathway product or derivative thereof, or another subsequent process that utilizes the furanic oxidation substrate. Typically, the furanic oxidation substrate is HMF.

To minimize production of undesired products, and maximize yield of the furanic oxidation substrate, it may be desirable to carry out the dehydration reaction to a partial conversion endpoint, as described in U.S. Patent Pub. No. 2017/0158656 (which is hereby expressly incorporated by reference in its entirety for all purposes), by quenching the reaction, and separating and recycling unconverted sugar, by, for example, filtration. When the furanic oxidation substrate is generated by the dehydration reaction, it is present in a dehydration product solution.

As used herein, the terms "dehydration product solution" or "crude oxidation feedstock" interchangeably refer to a solution comprising the furanic oxidation substrate and the dehydration solvent. The dehydration product solution can be a mixture that includes dissolved furanic oxidation substrate and one or more components that are not dissolved, wherein the one or more components that are not dissolved are selected from humin and unreacted sugar. The furanic oxidation substrate may be optionally separated from one or more components selected from the group consisting of a humin and an unreacted sugar and/or isolated from the dehydration product solution, and optionally further purified. In one such embodiment, the dehydration product solution is subjected to a membrane to effect the separation of the furanic oxidation substrate from one or more components selected from the group consisting of a humin and an unreacted sugar. Membranes suitable for use for such separation include nanofiltration membranes, or ultrafiltration membranes, or a combination thereof. The term "purified oxidation feedstock," for example a permeate solution, may be used to refer to the separated oxidation feedstock, and the term "retentate solution" may be used to refer to the separated solution with increased concentration of humins.

In some embodiments, selective membrane separation techniques (e.g., ultra-filtration and/or nano-filtration) are employed to separate unconverted fructose, intermediates and HMF from the other constituents of the combination withdrawn from the reaction zone. Selective membrane separation techniques utilized to treat the aqueous combination withdrawn from the reaction zone as disclosed herein provide effective recovery of unconverted fructose and intermediates for recycle, increased overall process yields and a high degree of product recovery.

In some embodiments, the aqueous reaction combination is contacted with one or more ultra-filtration membranes to produce a concentrate or retentate solution or stream containing at least a portion (preferably, substantially all) of the humins from the reaction combination and a permeate solution or stream containing unconverted fructose, intermediates, catalyst and HMF and depleted in humins relative to the aqueous reaction combination. The retentate stream may be then fed to a solvent and/or humin recovery unit for the recovery of solvent from the humins-containing retentate stream. The humins may be isolated as described in further detail herein, and the recovered solvent may be recycled.

Solvent and Humin Recovery

As the dehydration product solution is separated into a purified oxidation feedstock and a retentate solution subsequent to the sugar dehydration process, the retentate solution may be directed to a solvent recovery process. In some embodiments, the retentate solution comprises a retentate solvent and dissolved solids. In some embodiments, the retentate solvent comprises dehydration solvent, as described herein. In some embodiments, the retentate solvent is a multicomponent solvent. In some embodiments, the multicomponent solvent comprises water and a water-miscible aprotic organic solvent. In some embodiments, the water-miscible organic solvent is tetrahydrofuran, a glyme, dioxane, a dioxalane, dimethylformamide, sulfolane, acetone, N-methyl-2-pyrrolidinone, methyl ethyl ketone, or gamma-valerolactone or any combinations thereof. In some embodiments, the retentate solvent comprises 1,4-dioxane, water, or combinations thereof.

In some embodiments, the dissolved solids comprise a component of a carbohydrate feedstock, carbohydrate feedstock intermediate, carbohydrate feedstock byproduct, oxidation feedstock, an oxidation substrate, or combinations thereof. Compositions of carbohydrate feedstocks, carbohydrate feedstock intermediates, carbohydrate feedstock byproducts, oxidation feedstocks and oxidation substrates, are described herein. For example, in some embodiments, the dissolved solids comprise sugars such as C6 monosaccharides (e.g. glucose, fructose, or mannose), C5 monosaccharides (e.g. xylose, or arabinose), furan containing organic compounds (e.g. 5-hydroxymethylfurfural, 5-hydroxymethyl-2-furancarboxylic acid, 2,5-furandicarboxylic acid, furfural, 2-furoic acid, furfuryl alcohol, or furyl hydroxymethylketone), humins (e.g. polymerized sugars or dehydrated sugars, or polymerized furanic compounds), organic acids (e.g. levulinic acid, formic acid or acetic acid, and combinations thereof), homogenous acids (e.g. HCl, HBr, HI, $H_2SO_4$, $H_3PO_4$, oxalic acid, triflic acid, methane sulfonic acid, or boron trihalides, and combinations thereof), lithium, sodium, calcium, potassium or magnesium salts of the above-mentioned acids, or any combinations thereof. In some embodiments, the retentate solution comprises at least one of a humin, sugar, organic acid, furan containing organic compound, salt, or combinations thereof. In some embodiments, the salt is selected from the group consisting of sodium bromide, calcium bromide, sodium chloride, calcium chloride, potassium chloride, potassium chloride, magnesium chloride, magnesium chloride, and combinations thereof. In some embodiments, the salt is sodium bromide and/or calcium bromide or a mixture of both. In some embodiments, the salt is sodium chloride and/or calcium chloride or a mixture of both.

In some embodiments, retentate solution is further processed to form a depleted retentate stream with a decreased concentration of carbohydrate substrate and/or at least one dehydration pathway product from the retentate solution. In some embodiments, the depleted retentate solution is formed by further processing the retentate solution with a membrane. In some embodiments, HMF is removed from the retentate solution to form the depleted retentate solution. In some embodiments, the depleted retentate solution is enriched in humins, organic acids, or sugars, or any combinations thereof.

A feed solution, comprising the retentate solution and/or depleted retentate solution, may be fed into and processed by the solvent recovery process described herein. In some embodiments, the feed solution comprises or comprises about 1 wt %, 3 wt %, 5 wt %, 10 wt %, 15 wt %, 20 wt %, 25 wt %, 30 wt %, 31 wt %, 32 wt %, 35 wt %, 40 wt %, 50 wt % or 60 wt % of dissolved solids, or an amount that is within a range defined by any two of the aforementioned amounts. For example, in some embodiments, the feed solution comprises 5-40 wt % dissolved solids. In some embodiments, the feed solution has a pH of or about 0.5, 0.75, 1, 2, 3, 4, 5 or 6, or a pH that is within a range defined by any two of the aforementioned pHs. For example, in some embodiments, feed solution has a pH of or about 1-4. In some embodiments, the feed solution comprises a sugar concentration of or of about 15000, 20000, 22500, 25000, 28000, 30000, 31000, 35000, 40000, 50000, 60000, 70000, 80000, 90000, 100000, 110000, 120000, 150000, 200000, 250000, 300000 or 400000 ppm, or a concentration within a range defined by any two of the aforementioned concentrations. In some embodiments, the feed solution comprises a furanic compound concentration of or of about 1, 1.5, 2, 2.3, 2.5, 2.7, 3, 3.5, 4, 4.5, 5, 5.5, 6, 7 or 10 wt. %, or a concentration within a range defined by any two of the aforementioned concentrations. In some embodiments, the feed solution comprises a humin concentration of or of about 10000, 15000, 20000, 21000, 22000, 23000, 24000, 25000, 25300, 2600, 27000, 28000, 29000, 30000, 35000, 40000, 50000, 70000, 80000, 90000, 100000, 120000, 150000 or 200000 ppm, or a concentration within a range defined by any two of the aforementioned concentrations. In some embodiments, the feed solution comprises a concentration of organic acids of or of about 0.1, 0.15, 0.2, 0.24, 0.25, 0.3, 0.35, 0.4, 0.45, 0.5, 0.55, 0.6, 0.65, 0.7, 0.8, 0.9, 1 or 2 wt. %, or a concentration within a range defined by any two of the aforementioned concentrations. In some embodiments, the feed solution comprises a solvent concentration of or of about 50, 55, 60, 65, 68, 70, 75, 80, 82, 85, 88.9, 90, 92, 95, 98 or 99 wt. %, or a concentration within a range defined by any two of the aforementioned concentrations. In some embodiments, the feed solution comprises a dry residue concentration of or of about 5, 6, 7, 8, 10, 11.6, 12, 15, 17, 19, 20, 25 or 30 wt. %, or a concentration within a range defined by any two of the aforementioned concentrations.

The feed solution, comprising the retentate solution and/or depleted retentate solution, is subsequently processed to recover the retentate solvent and separately isolate the dissolved solids as a dry free-flowing powder. In some embodiments, the feed solution is processed by a thin film evaporator or a heated thin film evaporator. In some embodiments, the thin film evaporator or the heated thin film evaporator is orientated vertically, horizontally or diagonally or at a fixed angle with respect to the floor or the Earth's center of mass. In some embodiments, a vertically orientation is at or about at 0° of normal, and a horizontal orientation is at or about at 90° of normal. In some embodiments, the thin film evaporator or heated thin film evaporator is orientated at an angle between or between about 0° to 90° of normal or with respect to the floor, for example such as at or about at 5°, 10°, 15°, 30°, 45°, 60°, 75°, 80° or 85°, or any range of values there between. In some embodiments, the thin film evaporator or heated thin film evaporator is orientated at an angle of, at an angle of about, at an angle between or at an angle between about 0° to 180° such as at or about at 0°, 5°, 10°, 15°, 30°, 45°, 60°, 75°, 80°, 85°, 90°, 95°, 120°, 135°, 160° or 180°, or any range of values there between, wherein 0° corresponds to the thin film evaporator or heated thin film evaporator being oriented straight down, toward the Earth's center of mass and 180° corresponds to the thin film evaporator or heated thin film evaporator being oriented straight up, away from the Earth's center of mass. In some embodiments, the feed solution is processed by a horizontal thin film evaporator (HTFE) or a heated HTFE, for example an Artisan Rototherm® E Thin Film Evaporator. In some embodiments, the thin film evaporator system comprises a feed pump to direct the feed solution into the thin film evaporator. In some embodiments, the thin film evaporator system comprises a hot oil jacketed, counter-current horizontal thin-film evaporator. In some embodiments, the thin film evaporator system comprises condenser for solvent collection. In some embodiments, the thin film evaporator system comprises a vacuum pump. In some embodiments, the thin film evaporator system comprises a mass flow meter for inert gas sparge. In some embodiments, the thin film evaporator system comprises a bottom solid discharge valve. In some embodiments, the thin film evaporator system comprises a control system. In some embodiments, the control system is configured to maintain a thin film temperature, pressure, inert gas sparge, or feed rate, or combinations thereof of the thin film evaporator system.

Figure 1:
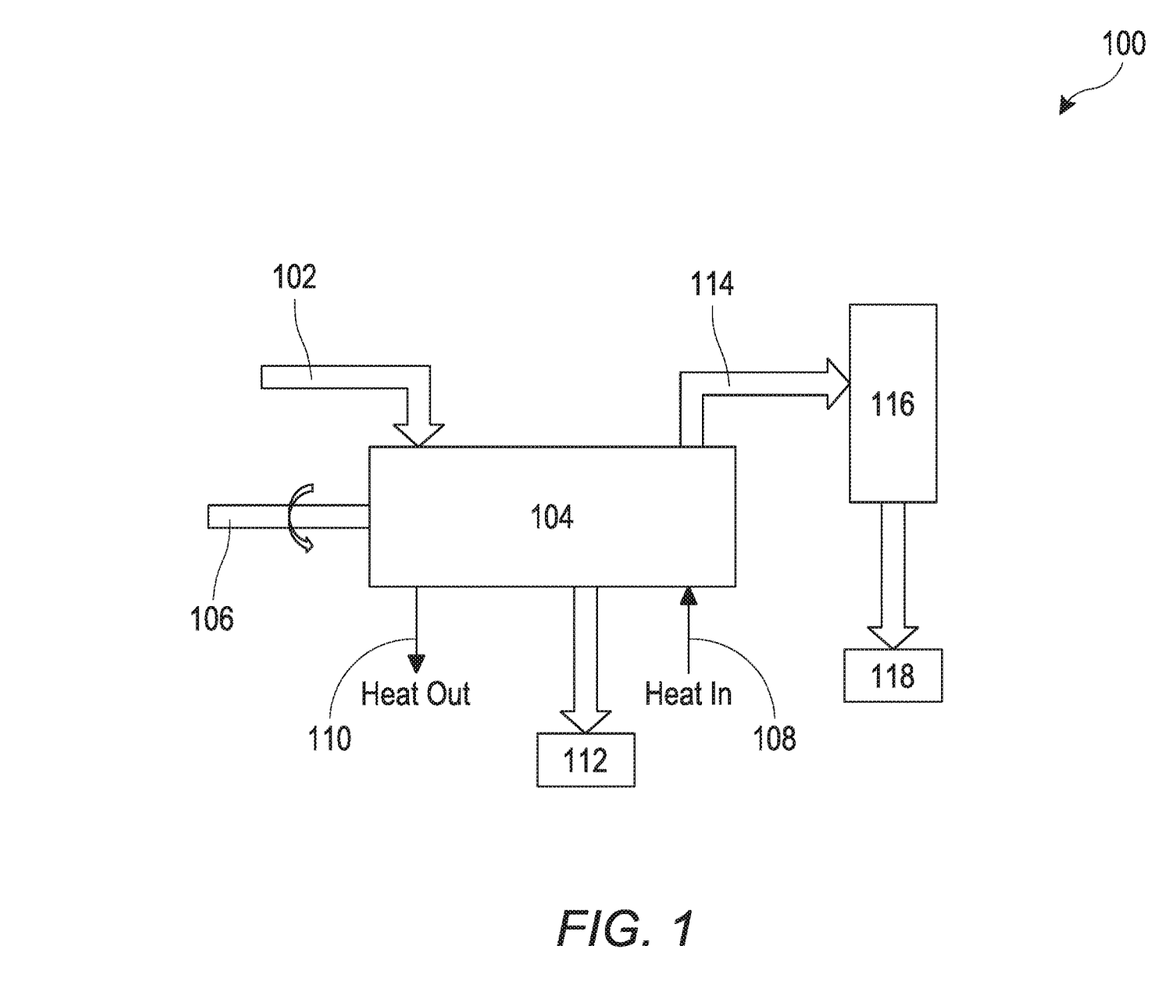
FIG. 1 illustrates a horizontal thin film evaporator (HTFE) and a method of use to process a retentate feed to obtain dry humin solids and collect solvent using a solvent condenser.
Figure 2:
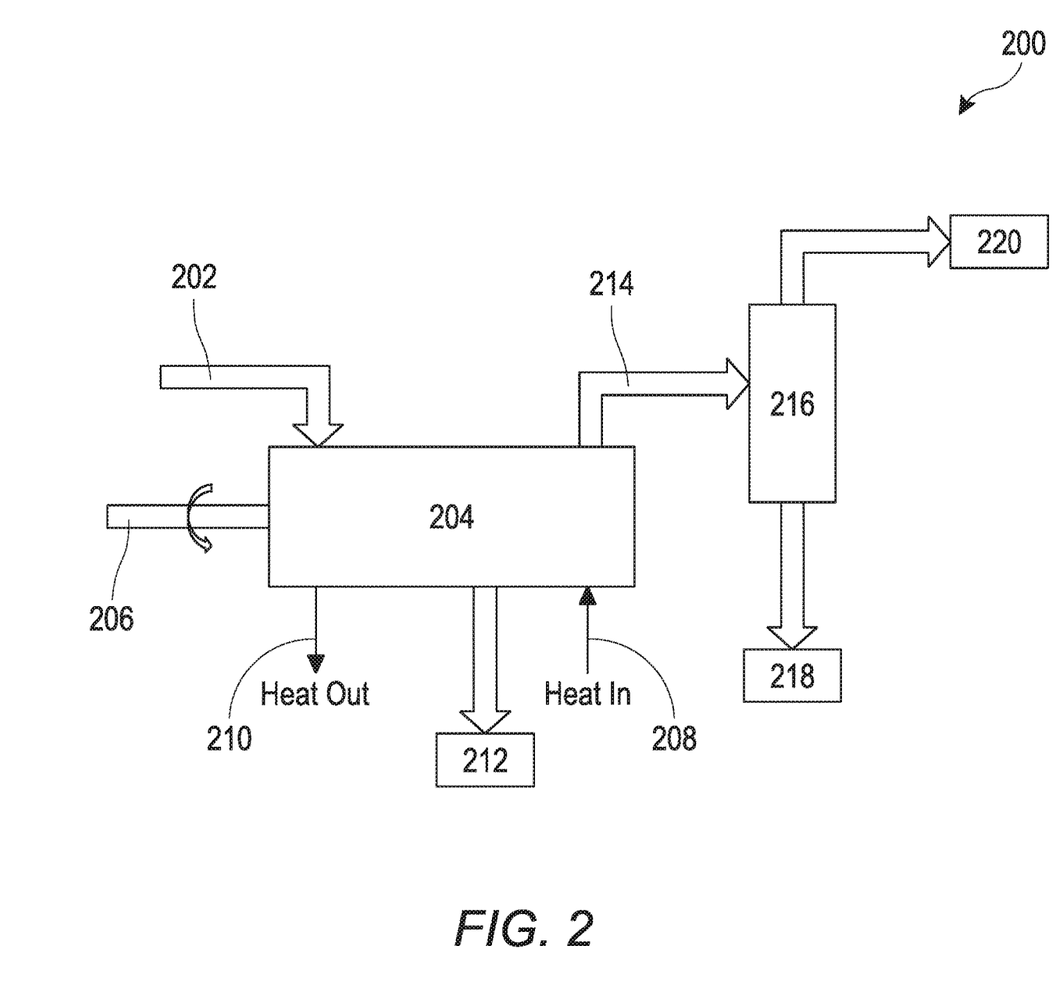
FIG. 2 illustrates a horizontal thin film evaporator (HTFE) and a method of use to process a retentate feed to obtain dry humin solids and collect purified solvent using continuous solvent distillation.

FIGS. 1 and 2 illustrate example uses of HTFEs to process a membrane retentate feed to obtain dry humin solids and collect solvent. FIG. 1 shows device 100, wherein a membrane retentate feed 102 directed into a HTFE 104. In some embodiments, the HTFE 104 is a counter-current HTFE. The HTFE 104 includes a rotating screw or wiper 106, a heat inlet 108 and a heat outlet 110. As the HTFE 104 operates with the addition of the membrane retentate feed 102, a dry free-flowing powder 112 is recovered from the processing of the membrane retentate feed 102. In some embodiments, the dry free-flowing powder 112 comprises dry humins. Furthermore, processing of the membrane retentate feed 102 by the HTFE 104 produces solvent vapors 114 directed to a solvent condenser 116, wherein the solvent condenser 116 produces a distillate 118.

FIG. 2 shows device 200, wherein a membrane retentate feed 202 directed into a HTFE 204. In some embodiments, the HTFE 204 is a counter-current HTFE. The HTFE 204 includes a rotating screw or wiper 206, a heat inlet 208 and a heat outlet 210. As the HTFE 204 operates with the addition of the membrane retentate feed 202, a dry free-flowing powder 212 is recovered from the processing of the membrane retentate feed 202. In some embodiments, the dry free-flowing powder 212 comprises dry humins. Furthermore, processing of the membrane retentate feed 202 by the HTFE 204 produces solvent vapors 214 directed to a continuous distillation column 216, wherein the solvent condenser 216 separately produces a bottoms collection 218 and a purified solvent distillate 220.

The feed solution is directed into the thin film evaporator, wherein the feed solution is held as a thin-film against the heated walls by a centrifugal force exerted by the rotor blades of the thin film evaporator, thereby causing the solvent to vaporize. As the feed solution is continuously directed into the thin film evaporator, the thin-film is continuously renewed and becomes progressively more concentrated with dissolved solids until the solids precipitate out of solution as solid products and are displaced towards the bottom discharge valve by the incoming feed. In some embodiments, the feed rate of the feed solution into the thin film evaporator is configured such that the residence time of the feed solution is below or below about 10, 5, 4, 3, 2, 1 or 0.5 minutes, or any range of values therebetween. In some embodiments, the feed rate is configured such that the residence time of the feed solution is below 2 minutes.

In some embodiments, the thin film evaporator is operated under an inert atmosphere inside the evaporator. An inert atmosphere may assist in generating a non-flammable atmosphere inside the evaporator. In some embodiments, the thin film evaporator is operated under a nitrogen flow. The feed concentration and solvent evaporation can be achieved under either atmospheric pressure or under vacuum. The feed can either be fed directly from a membrane separation unit or it can be pre-concentrated using standard evaporation technology to increase the dissolved solid content and to recover parts of the multi-component solvent mixture.

In some embodiments, the feed solution is introduced into the heated thin film evaporator having a thin-film temperature of or about 170, 175, 180, 185, 190, 195, 200, 205, 210, 215, 220, 225, 230, 235, 240 or 250° C., or any range of values therebetween. For example, in some embodiments, the thin-film temperature is between 180-230° C. In some embodiments, the thin film evaporator is operated at or at about 470, 480, 490, 500, 525, 550, 575, 600, 625, 650, 675, 700, 725, 750, 775, 800, 810, 820 or 850 torr pressure, or any range of values therebetween. For example, in some embodiments, the thin film evaporator is operated between 490-800 torr.

In some embodiments, the collected solvent vapors or distillate exiting the thin film evaporator may be fed into a condenser connected to the thin-film evaporator and collected, for example as illustrated in FIG. 1. In some embodiments, the collected solvent vapors or distillate exiting the thin film evaporator may be fed as vapors into a continuous distillation column to collect a continuous fractionation of solvents and light organic compounds, for example as illustrated in FIG. 2. In some embodiments, collected solvent distillate vapors may be further purified by fractionation distillation at ambient pressure to obtain a purified or isolated solvent mixture.

In some embodiments, the solvent distillate has a pH of or about 0.5, 0.75, 1, 2, 3, 4, 5 or 6, or any range of values therebetween. In some embodiments, the solvent distillate comprises a sugar concentration of or of about 1, 5, 10, 20, 30, 50, 100, 150, 200, 300, 400, 500, 600, 800 or 10000 ppm, or any range of values therebetween. In some embodiments, the solvent distillate comprises a furanic compound concentration of or of about 0.1, 0.2, 0.3, 0.4, 0.5, 0.6, 0.7, 0.8, 0.9, 1, 1.1, 1.2, 1.3, 1.4 1.5, 2, 2.3, 2.5, 2.7, 3, 3.5, 4, 4.5 or 5 wt. %, or any range of values therebetween. In some embodiments, the solvent distillate comprises a furanic compound concentration of or of about 50, 100, 500, 1000, 2000, 3000, 4000, 5000, 6000, 8000 or 10,000 ppm, or any range of values therebetween. In some embodiments, the solvent distillate comprises a humin concentration of or of about 200, 300, 400, 500, 600, 700, 800 or 900 ppm, or any range of values therebetween. In some embodiments, the solvent distillate comprises a concentration of organic acids of or of about <0.01, 0.01, 0.05, 0.1, 0.2, 0.3, 0.5, 0.7, 1, 1.2, 1.4, 1.5, 1.6, 1.7, 1.8, 1.9, 2, 2.5 or 3 wt. %, or any range of values therebetween. In some embodiments, the solvent distillate comprises a solvent concentration of or of about 2, 5, 10, 25, 50, 60, 70, 75, 80, 82, 85, 88.9, 90, 91, 92, 93, 94, 95, 96, 97, 98, 98.5, 99, 99.5, 99.8 or 99.9 wt. %, or any range of values therebetween. In some embodiments, the solvent distillate comprises a dry residue concentration of or of about 0.1, 0.3, 0.5, 0.6, 0.7, 0.8, 0.9, 1, 1.2, 1.5, 2, 3, 4, 5, 6, 7, 8 or 10 wt. %, or any range of values therebetween.

In some embodiments, the solvent distillate is subjected to a fractional distillation process to form fractional distillates. In some embodiments, the fractional distillates comprise an increase in concentration of organic solvent, water, furans, or organic acids, or any combinations thereof. In some embodiments, the solvent distillate recovers 70, 80, 85, 90, 92, 95, 97, 98, 99, 99.5 or 99.9% of organic solvent or an amount of solvent within a range defined by any two of the aforementioned percentages. In some embodiments, the organic solvent is a water-miscible aprotic organic solvent, as described herein. In some embodiments, the organic solvent is 1,4-dioxane.

In some embodiments, the bottom solid product discharged from the thin film evaporator is dry. In some embodiments, the solid product comprises a moisture content of, of about, less than or less than about 0.1, 0.33, 0.5, 0.62, 0.65, 1, 1.15, 1.88, 2, 3, 4 or 5 wt. %, or any range of values therebetween. In some embodiments, the solid product comprises a furan content of or of about 0.80, 0.85, 0.90, 0.92, 0.95, 0.96, 0.97, 0.98, 0.99, 1, 1.2 or 1.5 wt %, or any range of values therebetween. In some embodiments, the solid product comprises a sugar content of or of about 0.05, 0.1, 0.15, 0.17, 0.20, 0.5, 1, 1.3, 1.5, 1.6, 2, 3, 4, 4.5, 5, 6, 8 or 10 wt % or any range of values therebetween. In some embodiments, the solid product comprises an organic acid content of or of about 0.01, 0.05, 0.1, 0.2, 0.3, 0.4, 0.5, 0.6, 0.7, 0.8, 0.9, 1 or 2 wt. %, or any range of values therebetween. In some embodiments, the solid product comprises an organic solvent content of or of about 0.005, 0.01, 0.02, 0.03, 0.04, 0.05, 0.07, 0.1, 0.2, 0.3, 0.4, 0.5, 0.6, 0.7, 0.8, 0.9, 1 or 2 wt. %, or any range of values therebetween. In some embodiments, the solid product comprises a carbon content of or of about 50, 55, 56, 57, 58, 59, 60, 61, 62, 63, 65 or 70 wt. %, or any range of values therebetween. In some embodiments, the solid product comprises a hydrogen content of or of about 4, 4.2, 4.4, 4.5, 4.6, 4.7, 4.8, 4.9, 5 or 5.5 wt. %, or any range of values therebetween. In some embodiments, the solid product comprises a nitrogen content of or of about 0.1, 0.2, 0.3, 0.5, 0.8, 0.9, 1, 1.5 or 2 wt. %, or any range of values therebetween. In some embodiments, the solid product comprises a low sulfur content. In some embodiments, the solid product comprises a sulfur content of or of about 0, 0.1, 0.2, 0.3 or 0.5 wt. %, or any range of values therebetween. In some embodiments, the solid product comprises an oxygen content of or of about 20, 25, 28, 29, 30, 31, 32, 33, 34, 35 or 40 wt. %, or any range of values therebetween. In some embodiments, the solid product comprises a low ash content. In some embodiments, the solid product comprises an ash content when heated to 700° C. of or of about 0.1, 0.5, 1, 2, 3, 4, 5, 6, 7, 8, 10 or 15 wt. %, or any range of values therebetween. In some embodiments, the solid bottom product is a fine carbonaceous powder. In some embodiments, the solid product comprises a low metal content. In some embodiments, the solid product comprises a high humin content.

In some embodiments, the solid product may be subsequently washed, remaining solids filtered and the collected liquid dried to form a washed solid product. In some embodiments, the washed solid product comprises a reduced ash content relative to the unwashed solid product. In some embodiments, the washed solid product comprises a reduced salt content relative to the unwashed solid product. In some embodiments, the solid product is washed with at least one of water, an acid solution and/or an organic solvent. In some embodiments, the acidic solution comprises citric acid. In some embodiments, the organic solvent comprises ethanol. In some embodiments, the washed solid product comprises an ash content when heated to 700° C. of or of about 0.05, 0.1, 0.2, 0.3, 0.4, 0.5, 0.6, 0.7, 0.8, 0.9, 1 or 2 wt. %, or an amount that is within a range defined by any two of the aforementioned amounts.

In some embodiments, the solid product and/or washed product may be subsequently carbonized to form a carbonized solid product. In some embodiments, the carbonization process comprises exposing the product to high temperatures. In some embodiments, high temperatures may be selected from or from about 300, 400, 500, 600, 700, 800, 900, 1000, 1200, 1500 or 2000° C., or within a range defined by any two of the aforementioned temperatures. In some embodiments, the carbonization process comprises an inert atmosphere. In some embodiments, the inert atmosphere is a nitrogen atmosphere.

Additional Processing of Collected Products

In some embodiments, the collected products may be further processed for use in downstream applications. In some embodiments, the collected products comprise solid products, washed solids products, or carbonized products, or any combinations thereof. In some embodiments, collected products are further processed into a desired product. In some embodiments, the desired products may be used for soil applications (e.g., soil amendments or fertilizers), energy storage applications or for liquid and gas purification applications. In some embodiments, the desired product may be a soil conditioner, soil enhancer, soil amendment, soil purifier, fertilizer, anode material, or activated carbon material.

In some embodiments, the desired product is an activated carbon material. In some embodiments, the activated carbon material may be used for gas purification, liquid purification or electrode material applications. In some embodiments, the activated carbon material comprises a surface area of at least or at least about 800, 900, 1000, 1200, 1400, 1600, 1800 or 2000 m$^2$/g, or a surface area that is within a range defined by any two of the aforementioned surface areas. In some embodiments, the activated carbon material is a powder activated carbon, or a granular or pellet activated carbon. In some embodiments, forming a powder activated carbon from solid products comprises washing the solid product as described herein, high temperature carbonization of the washed solid product as described herein, and activation of carbonized solid product. In some embodiments, activation of the solid product comprises steam and/or gas activation. In some embodiments, steam and/or gas activation comprises exposing the solid product to high temperatures under a steam or combustion gas atmosphere. In some embodiments, the combustion gas atmosphere comprises $CO_2$, CO, or $N_2$, or combinations thereof. In some embodiments, the high temperature used in steam and gas activation is or is about 600, 700, 800, 900, 1000, 1100 or 1200° C., or within a range defined by any two of the aforementioned temperatures. In some embodiments, activation of the solid product comprises chemical activation. In some embodiments, chemical activation comprises mixing the solid product with a strong base followed by exposure to high temperatures in an inert atmosphere. In some embodiments, the strong base may be KOH, or NaOH, or combinations thereof. In some embodiments, the high temperature used in chemical activation is or is about 400, 500, 600, 700, 800, 900 or 1000° C., or within a range defined by any two of the aforementioned temperatures. In some embodiments, additional milling of the activated particles are performed to obtain desired particle sizes.

In some embodiments, a granular or pellet activated carbon is formed by the same process as forming powdered activated carbon, except that subsequent to the washing process and prior to the high temperature carbonization process the washed solid product is subjected to a granulation or compaction process. In some embodiments, forming a granular or pellet activated carbon comprises washing the solid product, as described herein, blending the washed solid product with a bio-based binder, extrusion, pelletization or granulation of the binder-solid product mixture, a subsequent drying or oxidation, a subsequent optional exposure to a high temperature carbonization process, as described herein, a subsequent activation of the carbonized solid product, as described herein, and a subsequent washing and drying the activated product. In some embodiments, the bio-based binder is tall oil pitch, an aqueous mixture of a sugar and/or cellulose derivative, or combinations thereof. In some embodiments, the cellulose derivative is hydroxyethylcellulose. In some embodiments, drying or oxidation is performed in air at 100, 150, 200, 250 or 300° C., or within a range defined by any two of the aforementioned temperatures.

In some embodiments, the desired product is a hard carbon material. In some embodiments, the hard carbon material may be used in energy storage applications, for example as anode materials in lithium-ion batteries. In some embodiments, hard carbon materials are characterized by a low surface area relative to the solid product starting material. In some embodiments, forming a hard carbon material from solid products comprises washing the solid product as described herein, high temperature carbonization of the washed solid product as described herein, milling and classification of the carbonized product, and coating and post-carbonization processing the milled product.

FDCA Pathway Process

In the present disclosure, any and all FDCA pathway processes may be utilized. As used herein, the terms "furandicarboxylic acid pathway product" and "FDCA pathway product" are used interchangeably herein to refer to 2,5-furandicarboxylic acid (FDCA) or a 2,5-furandicarboxylic acid pathway intermediate compound.

In some embodiments, the FDCA pathway product is FDCA. In some embodiments, the oxidation substrate is a sugar, HMF, and/or an FDCA pathway intermediate compound (e.g., DFF, HMFCA, or FFCA), or a mixture of any two or more thereof. In some embodiments, the oxidation feedstock may further contain other agents or residual components that are soluble or insoluble in the oxidation feedstock. For example, the oxidation feedstock may be a crude oxidation feedstock of HMF, or other oxidation substrate, and the oxidation solvent. The term "crude oxidation feedstock" refers herein to a feedstock which, in addition to comprising the desired oxidation substrate, also comprises impurities and/or by-products related to the production, isolation, and/or purification of the desired oxidation substrate. For example, the oxidation feedstock, may, in addition, comprise certain biomass-related components that originate from biomass or are by-products, which are generated in the conversion of biomass to a sugar (by, for example, thermal, chemical, mechanical, and/or enzymatic degradative approaches), whereby such sugar is subsequently converted to HMF. Thus, the crude oxidation feedstock may also comprise a component selected from the group consisting of a polysaccharide (including, for example, a cellulose (e.g., a lignocellulose, or a hemicellulose, and the like), or starch, and the like), or an oligosaccharide (e.g., a raffinose, a maltodextrin, or a cellodextrin, and the like), or a monosaccharide (e.g., glucose, fructose, galactose, mannose, xylose, or arabinose, and the like), or a disaccharide (e.g., sucrose, lactose, maltose, or cellobiose and the like), or furanic substrates such as, furfural, oligomeric or polymeric humin by-products (humins) or residual mineral acids, or salts of the corresponding mineral acids. Similarly, the oxidation feedstock may be a crude feedstock of HMF oxidation products comprising HMF and/or FDCA pathway intermediate compounds. The crude oxidation feedstock may be processed to increase the concentration of the desired oxidation substrate and/or decrease the concentration of impurities and/or by-products, wherein the crude oxidation feedstock processed in this way may be referred to as a "purified oxidation feedstock," as described herein.

As used herein, the term, "oxidation solvent" refers to a solvent that is an organic solvent or a multi-component solvent in which the oxidation substrate and the desired FDCA pathway product are each separately soluble at a minimum level of at least 2% by weight at the temperature at which the contacting (oxidation) step is conducted. Typically, the oxidation solvent is one in which the FDCA pathway product has a solubility of at least 3 wt %, at least 4 wt %, and more typically, at least 5 wt %, at least 6 wt %, at least 7 wt %, at least 8 wt %, at least 9 wt %, at least 10 wt %, at least 11 wt %, at least 12 wt %, at least 13 wt %, at least 14 wt %, or at least 15 wt %, or a solubility within a range defined by any two of the aforementioned amounts, as measured at the temperature at which the contacting step is carried out. In some embodiments, the FDCA pathway product has a solubility that ranges from between 2-4 wt %, 3-5 wt %, 4-6 wt %, 5-7 wt %, 6-8 wt %, 7-9 wt %, 8-10 wt %, 9-11 wt %, 10-12 wt %, 11-13 wt %, 12-14 wt %, or 13-15% or is within a range defined by any of two of the aforementioned weight percentages. The solubility of the FDCA pathway product in a candidate organic solvent or candidate multi-component solvent can be readily determined using known methods.

Organic solvents that exhibit the requisite minimal solvating requirements for the oxidation substrate and FDCA are suitable for use, either alone or as a component of a multi-component solvent. In some embodiments, the oxidation solvent comprises an aprotic organic solvent (e.g., an ether, an ester, or a ketone, and the like) either alone (i.e., as a single-component solvent) or as a component of a multi-component solvent. When used in a multi-component solvent, the aprotic organic solvent is typically miscible with the other component(s) of the multi-component solvent. The term "multi-component solvent" refers herein to a mixture of two, three, or more solvent species. Multi-component solvents employed in the practice of the present disclosure may comprise two or more solvent species selected from the group consisting of a first organic solvent species, a second organic solvent species, and water. When the multi-component solvent comprises water and an organic solvent, the organic solvent is a water-miscible organic solvent. Typically, the water-miscible organic solvent is a water-miscible aprotic organic solvent.

In some embodiments, candidate component solvents for the multi-component solvent are not be limited to solvents in which the oxidation substrate and desired FDCA pathway product are highly soluble, as multi-component solvents may exhibit a synergistic solvating effect with respect to FDCA, even when FDCA is poorly soluble in each component solvent. For example, FDCA has poor solubility in water. However, even when paired with a water-miscible organic solvent having poor FDCA-solvating capabilities, the combination of water and the water-miscible organic solvent exhibits enhanced FDCA-solvating capability.

Illustrative multi-component solvents that exhibit this effect include those that comprise water and a water-miscible aprotic organic solvent. Exemplary water-miscible aprotic solvents suitable for use in the practice of the present disclosure include tetrahydrofuran, a glyme, dioxane, a dioxolane, dimethylformamide, dimethylsulfoxide, sulfolane, acetone, N-methyl-2-pyrrolidone ("NMP"), methyl ethyl ketone ("MEK"), or gamma-valerolactone, and the like. Preferably, the water-miscible aprotic organic solvent is an ether, such as, for example, a glyme, dioxane (1,4-dioxane), a dioxolane (e.g., 1,3-dioxolane), or tetrahydrofuran, and the like. Glymes that are suitable for use in the practice of the present disclosure include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, or a highly ethoxylated diether of a high molecular weight alcohol ("higlyme"), and the like. Often, the oxidation solvent is a multi-component solvent comprising water and a water-miscible aprotic organic solvent that is glyme, diglyme, or dioxane.

In some embodiments, the composition of the oxidation solvent may take into consideration the requirements of further downstream processes (e.g., to facilitate product recovery, purification, and the like), or upstream processes (e.g., the conversion of a sugar to the furanic oxidation substrate). For example, in certain embodiments it may be desirable to employ an oxidation solvent that is a multi-component solvent comprising a light solvent and a heavy solvent. The term "light solvent" refers to a solvent having a boiling point at a certain pressure that occurs at a temperature that is less than the boiling point (temperature) of the heavy solvent at the same pressure. Conversely, the term "heavy solvent" refers to a solvent having a boiling point at a certain pressure that occurs at a temperature that is higher than the boiling point (temperature) of the light solvent at the same pressure. When the multi-component solvent comprises water and a water-miscible organic solvent, the water-miscible organic solvent may be a light water-miscible organic solvent (e.g., a water-miscible organic solvent having a boiling point that occurs at a temperature less than the boiling point of water) or it may be a heavy water-miscible organic solvent (e.g., a water-miscible organic solvent having a boiling point that occurs at a temperature higher than the boiling point of water). Typically, the light and heavy water-miscible organic solvent are a light and heavy aprotic organic solvent, respectively. Exemplary light water-miscible (and aprotic) organic solvents employed with water in a multi-component solvent include, for example, glyme, a dioxolane (e.g., 1,3-dioxolane), or tetrahydrofuran, and the like. Exemplary heavy water-miscible (and aprotic) organic solvents employed with water in a multi-component solvent include, for example, dioxane, ethyl glyme, diglyme (diethylene glycol dimethyl ether), ethyl diglyme, triglyme, butyl diglyme, tetraglyme, or a polyglyme, and the like. In some embodiments (e.g., continuous reactor systems), all or a portion of the oxidation solvent or component thereof may be removed from the production solution (e.g., via distillation) and recycled to the reaction mixture. It such embodiments, it may be desirable to employ a multi-component solvent having a composition that corresponds to an azeotrope or which is capable of forming an azeotrope (i.e., an "azeotropic composition") at a temperature employed during the oxidation step (i.e., contacting step), or at a temperature employed during a process that is upstream or downstream of the oxidation step. Use of such multi-component solvents having an azeotropic composition may facilitate the recycling of the oxidation solvent (as part of the azeotropic composition) to the oxidation step, or to processes that occur upstream and/or downstream of the oxidation step.

In some embodiments, the water-miscible organic solvent species is at least 5 volume % (vol %), at least 10 vol %, at least 15 vol %, at least 20 vol %, at least 25 vol %, at least 30 vol %, at least 35 vol %, at least 40 vol %, at least 45 vol %, at least 50 vol %, at least 55 vol %, at least 60 vol %, at least 65 vol %, at least 70 vol %, at least 75 vol %, at least 80 vol %, at least 85 vol %, at least 90 vol %, or at least 95 vol % of the multi-component solvent; and correspondingly, water is typically less than 95 vol %, less than 90 vol %, less than 85 vol %, less than 80 vol %, less than 75 vol %, less than 70 vol %, less than 65 vol %, less than 60 vol %, less than 55 vol %, less than 50 vol %, less than 45 vol %, less than 40 vol %, less than 35 vol %, less than 30 vol %, less than 25 vol %, less than 20 vol %, less than 15 vol %, less than 10 vol %, or less than 5 vol %, respectively, of the multi-component system.

In some embodiments, the multi-component solvent comprises water in a range from or any number in between 1-5 wt % and a water-miscible organic solvent in a range from or any number in between 99-95 wt %. In some embodiments, the multi-component solvent comprises water in a range from or any number in between 5-10 wt % and a water-miscible organic solvent in a range from or any number in between 95-90 wt %. In some embodiments, the multi-component solvent comprises water in a range from or any number in between 10-15 wt % and a water-miscible organic solvent in a range from or any number in between 90-85 wt %. In some embodiments, the multi-component solvent comprises water in a range from or any number in between 15-20 wt % and a water-miscible organic solvent in a range from or any number in between 85-80 wt %. In some embodiments, the multi-component solvent comprises water in a range from or any number in between 20-25 wt % and a water-miscible organic solvent in a range from or any number in between 80-75 wt %. In some embodiments, the multi-component solvent comprises water in a range from or any number in between 25-30 wt % and a water-miscible organic solvent in a range from or any number in between 75-70 wt %. In some embodiments, the multi-component solvent comprises water in a range from or any number in between 30-35 wt % and a water-miscible organic solvent in a range from or any number in between 70-65 wt %. In some embodiments, the multi-component solvent comprises water in a range from or any number in between 35-40 wt % and a water-miscible organic solvent in a range from or any number in between 65-60 wt %. In some embodiments, the multi-component solvent comprises water in a range from or any number in between 40-45 wt % and a water-miscible organic solvent in a range from or any number in between 60-55 wt %. In some embodiments, the multi-component solvent comprises water in a range from or any number in between 45-50 wt % and a water-miscible organic solvent in a range from or any number in between 65-50 wt %. In some embodiments, the multi-component solvent comprises water in a range from or any number in between 50-55 wt % and a water-miscible organic solvent in a range from or any number in between 50-45 wt %. In some embodiments, the multi-component solvent comprises water in a range from or any number in between 55-60 wt % and a water-miscible organic solvent in a range from or any number in between 45-40 wt %. In some embodiments, the multi-component solvent comprises water in a range from or any number in between 60-65 wt % and a water-miscible organic solvent in a range from or any number in between 40-35 wt %. In some embodiments, the multi-component solvent comprises water in a range from or any number in between 65-70 wt % and a water-miscible organic solvent in a range from or any number in between 35-30 wt %. In some embodiments, the multi-component solvent comprises water in a range from or any number in between 70-75 wt % and a water-miscible organic solvent in a range from or any number in between 30-25 wt %. In some embodiments, the multi-component solvent comprises water in a range from or any number in between 75-80 wt % and a water-miscible organic solvent in a range from or any number in between 25-20 wt %. In some embodiments, the multi-component solvent comprises water in a range from or any number in between 80-85 wt % and a water-miscible organic solvent in a range from or any number in between 20-15 wt %. In some embodiments, the multi-component solvent comprises water in a range from or any number in between 85-90 wt % and a water-miscible organic solvent in a range from or any number in between 15-10 wt %. In some embodiments, the multi-component solvent comprises water in a range from or any number in between 90-95 wt % and a water-miscible organic solvent in a range from or any number in between 10-5 wt %. In some embodiments, the multi-component solvent comprises water in a range from or any number in between 95-99 wt % and a water-miscible organic solvent in a range from or any number in between 5-1 wt %.

In some embodiments, the volume ratio of water to water-miscible organic solvent is in the range from or any number in between 1:6 to 6:1. In certain embodiments, the volume ratio is from or any number in between 1:4 to 4:1 water:water-miscible organic solvent. In other embodiments, the volume ratio is from or any number in between 1:4 to 3:1 water:water miscible organic solvent. In other embodiments, the volume ratio is from or any number in between 1:3 to 3:1 water:water miscible organic solvent. In certain embodiments, the volume ratio is 1:1 water:water-miscible organic solvent.

In some embodiments, the multi-component solvent comprises water and two different water-miscible organic solvents. Typically both of the water-miscible organic solvents are water-miscible aprotic organic solvents. Each of the two water-miscible aprotic solvents can be independently selected from the group of tetrahydrofuran, a glyme, a dioxane, a dioxolane, dimethylformamide, dimethylsulfoxide, sulfolane, acetone, N-methyl-2-pyrrolidone ("NMP"), methyl ethyl ketone ("MEK"), or gamma-valerolactone. One or both of the water-miscible aprotic organic solvent can be an ether, such as, for example, a glyme, dioxane (for example 1,4-dioxane), dioxolane (e.g., 1,3-dioxolane), or tetrahydrofuran, and the like. Glymes include, for example, monoglyme (1,2-dimethoxyethane, "DME"), ethyl glyme, diglyme (diethylene glycol dimethyl ether), ethyl diglyme, triglyme, butyl diglyme, tetraglyme, a polyglyme, or a highly ethoxylated diether of a high molecular weight alcohol ("higlyme"), and the like.

In some embodiments, the volume ratio of water to the first and second water-miscible organic solvent is approximately 1:1:1 (v:v:v). In some embodiments, the volume ratio of water to the first and second water-miscible organic solvent is approximately 1:2:1 (v:v:v). In some embodiments, the volume ratio of water to the first and second water-miscible organic solvent is approximately 1:2:2 (v:v:v). In some embodiments, the volume ratio of water to the first and second water-miscible organic solvent is approximately 2:1:1 (v:v:v).

In some embodiments, oxidation catalysts employed to oxidize the oxidation substrate into an FDCA pathway product, and typically have the noble metal dispersed on the internal and/or external surfaces of the support. The term "noble metal" refers herein to ruthenium, rhodium, palladium, silver, osmium, iridium, platinum or gold. In some embodiments, the metal is selected from the group consisting of platinum, gold, and a combination thereof. In some embodiments, the metal is platinum. In some embodiments, the metal is gold. The heterogeneous oxidation catalyst may further include a promoter to enhance the performance of the heterogeneous oxidation catalyst. When the metal is platinum, gold, or combination thereof, suitable promoters include, for example, Pd, Ir, Mo, Bi, Te, Sn or W, and the like.

The solid support component of the oxidation catalyst may comprise any type of material known by those having ordinary skill in the art as being suitable for use as a catalytic support that also has the specific surface area requirement described herein. In some embodiments, suitable materials include, for example, a metal oxide, a carbonaceous material, a polymer, a metal silicate, a metal carbide, or any composite material prepared therefrom. Exemplary metal oxides include silicon oxide (silica), zirconium oxide (zirconia), titanium oxide (titania), or aluminum oxide (alumina), and the like. As used herein, the term "carbonaceous" refers to graphite and carbon black. Exemplary metal silicates include, for example, an orthosilicate, a borosilicate, or an aluminosilicate (e.g., a zeolite), and the like. Exemplary metal carbides include, for example, silicon carbide, and the like. Suitable polymeric solid support materials include polystyrene, polystyrene-co-divinyl benzene, polyamides, or polyacrylamides, and the like.

In carrying out the FDCA pathway process, oxygen may be provided in neat form (i.e., $O_2$ only, with no other gases) or as a component of a mixture of gases (e.g., air, oxygen-enriched air, oxygen depleted air, oxygen mixed in nitrogen and the like). The molar ratio of oxygen to the oxidation substrate during the contacting step is typically in the range of from 2:1 to 10:1. In some embodiments, the molar ratio of oxygen to the oxidation substrate is from 2:1 to 10:1, or from 3:1 to 5:1. During the contacting step, oxygen is typically present at a partial pressure in the range of from or any number in between 40 psig to 1000 psig. More typically, oxygen is present at a partial pressure in the range of from or any number in between 40 psig to 200 psig. In some embodiments, oxygen is present at a partial pressure in the range from or any number in between 40-200 psig, 100-300 psig, 200-400 psig, 300-500 psig, 400-600 psig, 500-700 psig, 600-800 psig, 700-900 psig, or 800-1000 psig, or within a range defined by any two of the aforementioned partial pressures.

In some embodiments, the oxidation of the oxidation substrate to the FDCA pathway product is carried out at a temperature in the range of from or any number in between 50° C. to 200° C. In some embodiments, the oxidation step is carried out at a temperature in the range of from or any number in between 80° C. to 180° C., and in other embodiments, the oxidation step carried out at a temperature in the range from or any number in between 90° C. to 160° C. or from or any number in between 100° C. to 160° C. In some embodiments, the oxidation step is carried out at a temperature in the range of from or any number in between 90° C. to 180° C., and sometimes it is carried out at a temperature in the range of from or any number in between 110° C. to 160° C.

The processes of the present disclosure may be carried out in batch, semi-batch, or continuous reactor format using reactors known in the art, such as, for example, fixed bed reactors, trickle bed reactors, slurry phase reactors, or moving bed reactors, and the like. The relatively high solubilities of reactants and products (particularly, the FDCA pathway product) in the oxidation solvent facilitate the use of all such reactor formats, and particularly the fixed bed reactor format.

An FDCA pathway product(s) may be recovered from the reaction mixture by separating a catalyst used to form the FDCA pathway product from a product solution comprising the FDCA pathway product(s) and the oxidation solvent. The product solution includes the oxidation solvent and soluble components of the reaction mixture and excludes the catalyst. The product solution may be further concentrated with respect to the soluble components by removal of a portion of the oxidation solvent. Oxidation solvent removal may be accomplished by evaporation (e.g., by using an evaporator), or distillation, and the like.

Alternatively, or further to the isolation step, the FDCA pathway product may be purified. Preferably, the FDCA pathway product is purified by crystallization. Purification and crystallization of the FDCA pathway product can be accomplished using known methods. Separation of the FDCA pathway product crystals from the crystallization solvent can be accomplished using known methods for separating solids from liquids, such as, for example, filtration, or centrifugation, or both.

EXAMPLES

Various exemplary embodiments of a thin-film evaporator process used to separate and recover process solvents and solid organic impurities from a byproduct enriched membrane retentate stream obtained from a dehydration process are described herein.

General Analytical Methods

The humin content in all streams were determined using UV-vis spectrophotometric methods (absorbance in 360-460 nm range) using precipitated humins as a reference standard. Furan-containing compounds were determined using HPLC-UV methods using known, commercial compounds as reference standards. Water content was determined using Karl-Fischer titration. 1,4-Dioxane content was determined using GC methods with commercial 1,4-dioxane as reference standard. Organic acids were determined using HPLC-UV methods with commercial compounds as reference standards. Dry residue was determined by freeze-drying samples and recording the residual weight. Residual moisture content of collected bottom fractions was determined gravimetrically by heating a sample to 105° C. until a constant weight was obtained. Residual organic compounds in collected solid fractions were determined by stirring the solid sample (1 g) in deionized water (20 g) and analyzing the water phase after filtration with above mentioned methods. The ash content of collected solids was determined gravimetrically by heating a sample to 700° C. in ambient air flow. CHNSO was analyzed using a Thermo Flash 2000 organic elemental analyzer.

Example 1

Example 1 describes the solvent and solid separation and recovery of a feed processed through a thin film evaporator. The feed comprised humins, sugars, organic acids, furan containing organic compounds, and sodium bromide, as well as, a 1,4-dioxane and water multicomponent solvent. The feed was introduced into the thin-film evaporator at various feed rates and thin-film temperatures. The distillate and dry bottom fractions were collected in dry, pre-weighted glass containers for each timed run.

The test setup used the following main equipment, where all process-wetted metal parts were 316 stainless steel: peristaltic feed pump; 465 cm² (interior), hot oil jacketed, counter-current horizontal thin-film evaporator with motor driven rotor, 5 cm bottom outlet and 5 cm vapor outlet; 0.37 m² (interior) U-tube condenser, vapor on shell side, chilled water on the tube side; dry ice cold trap to condense vapor bypass; vacuum pump; and mass flow meter for nitrogen sparge. Equipment setup parameters for Test Runs 1-1 through 1-7 are shown in Table 1 herein.

TABLE 1

| | Parameters | | | | | | |
|---|---|---|---|---|---|---|---|
| Tests | 1-1 | 1-2 | 1-3 | 1-4 | 1-5 | 1-6 | 1-7 |
| Thin film (° C.) | 189 | 195 | 198 | 203 | 186 | 196 | 198 |
| Pressure (torr) | 753 | 753 | 753 | 753 | 757 | 757 | 757 |
| $N_2$ sparge (L/min, STP) | 9.5 | 9.5 | 9.5 | 9.5 | 9.5 | 9.5 | 9.5 |
| Feed rate (g/min) | 82 | 98 | 115 | 131 | 98 | 98 | 115 |
| Distillate rate (g/min) | 46 | 81 | 95 | 116 | 74 | 73 | 85 |
| Bottoms rate (g/min) | 33 | 13 | 14 | 6 | 9 | 13 | 10 |
| Total collected (g/min) | 79 | 94 | 109 | 122 | 83 | 86 | 95 |
| Mass balance (%) | 96 | 96 | 95 | 93 | 85 | 88 | 83 |
| Evaporation (%) | 56 | 83 | 83 | 89 | 76 | 75 | 73 |

Analytical data of the feed material (Feed-1) and solvent distillates for Test Runs 1-1 through 1-7 are shown in Table 2 herein:

TABLE 2

| | Feed and Solvent Distillates | | | | | | |
|---|---|---|---|---|---|---|---|
| Tests | pH | Density (g/mL) | Sugars (ppm) | Furans (wt %) | Humins (ppm) | Organic acids (wt %) | Solvent (wt %) | Dry residue (wt %) |
| Feed-1 | 2.0 | 1.09 | 110000 | 2.3 | 25000 | 0.65 | 82.0 | 19.0 |
| Solvent 1-1 | 2.3 | 1.04 | 400 | 1.53 | 598 | 1.96 | 91.6 | 3.53 |
| Solvent 1-2 | 2.2 | 1.04 | 500 | 1.2 | 438 | 1.83 | 93.3 | 3.11 |
| Solvent 1-3 | 2.2 | 1.03 | 400 | 1.47 | 564 | 1.79 | 92.2 | 3.34 |
| Solvent 1-4 | 2.3 | 1.04 | 400 | 1.03 | 361 | 1.51 | 96.5 | 2.61 |
| Solvent 1-5 | 2.2 | 1.03 | 500 | 1.24 | 424 | 1.65 | 95.0 | 2.97 |
| Solvent 1-6 | 2.2 | 1.04 | 400 | 1.0 | 394 | 1.60 | 94.7 | 2.67 |
| Solvent 1-7 | 2.2 | 1.04 | 500 | 1.37 | 683 | 1.98 | 90.4 | 3.44 |

Analytical data of the solid bottom fractions for Test Runs 1-2 and 1-3 are shown herein in Table 3 as Solid 1-2 and 1-3, respectively.

TABLE 3

| | Solid Bottom Fractions | | | | | |
|---|---|---|---|---|---|---|
| Sample | Moisture (wt %) | Furans (wt %) | Sugars (wt %) | Dioxane (wt %) | C/H/N/S/O (wt %) | Ash, 700° C. (wt %) |
| Solid 1-2 | 0.65 | 0.92 | 1.6 | 0.034 | — | — |
| Solid 1-3 | 0.33 | 0.98 | 2.0 | 0.022 | 57.9/4.9/1.0/0/29.9 | 5.0 |

Example 2

Example 2 describes the solvent and solid separation and recovery of a feed processed through a thin film evaporator. The feed comprises humins, sugars, organic acids, furan containing organic compounds, and sodium bromide, as well as, a 1,4-dioxane and water multicomponent solvent. The feed was introduced into the thin-film evaporator at various feed rates, thin-film temperatures, nitrogen sparge rates, and reactor pressures. The distillate and dry bottom fractions were collected in dry, pre-weighted glass containers for each timed run.

The test setup used the following main equipment, where all process-wetted metal parts were 316 stainless steel: 300 L agitated feed tank; peristaltic feed pump; 930 cm² (interior), hot oil jacketed, counter-current horizontal thin-film evaporator with motor driven rotor, 10 cm bottom outlet and 10 cm vapor outlet; 0.7 m² (interior) U-tube condenser, vapor on shell side, chilled water on the tube side; Dry ice cold trap to condense vapor bypass; Vacuum pump; and Mass flow meter for nitrogen sparge. Equipment setup parameters for Test Runs 2-1 through 2-6 are shown in Table 4 herein.

TABLE 4

| | Parameters | | | | | |
|---|---|---|---|---|---|---|
| Run | 2-1 | 2-2 | 2-3 | 2-4 | 2-5 | 2-6 |
| Thin film (° C.) | 202-210 | 224 | 221 | 216 | 219 | 228 |
| Pressure (torr) | 749 | 500 | 498 | 500 | 500 | 505 |
| $N_2$ sparge (L/min, STP) | 14.3 | 1.9 | 1.9 | 1 | 1 | 1 |
| Feed rate (g/min) | 214 | 182 | 182 | 182 | 182 | 182 |
| Distillate rate (g/min) | 215 | 157 | 157 | 180 | 176 | 177 |

TABLE 4-continued

| | Parameters | | | | | |
|---|---|---|---|---|---|---|
| Run | 2-1 | 2-2 | 2-3 | 2-4 | 2-5 | 2-6 |
| Bottoms rate (g/min) | 9 | 17 | 14 | 10 | 2.4 | 9 |
| Total collected (g/min) | 224 | 174 | 171 | 190 | 178.4 | 186 |
| Mass balance (%) | 105 | 96 | 94 | 104 | 98 | 102 |
| Evaporation (%) | 100 | 86 | 86 | 99 | 97 | 97 |

Analytical data of the feed material (Feed-2) and solvent distillates for Test Runs 2-1 through 2-6 are shown in Table 5 herein:

TABLE 5

| | Feed and Solvent Distillates | | | | | | |
|---|---|---|---|---|---|---|---|
| Sample | pH | Density (g/mL) | Sugars (ppm) | Furans (wt %) | Humins (ppm) | Organic acids (wt %) | Solvent (wt %) | Dry residue (wt %) |
| Feed-2 | 2.2 | 1.07 | 31000 | 4.5 | 25300 | 0.24 | 88.9 | 11.6 |
| Solvent 2-1 | 2.6 | 1.04 | 21 | 0.47 | 335 | 0.29 | 98.7 | 0.67 |
| Solvent 2-2 | 2.6 | 1.04 | 10 | 0.76 | 269 | 0.19 | 98.5 | 0.74 |
| Solvent 2-3 | 2.5 | 1.04 | 23 | 0.80 | 447 | 0.23 | 98.3 | 1.04 |
| Solvent 2-4 | 2.5 | 1.04 | 34 | 0.67 | 455 | 0.24 | 98.8 | 0.88 |
| Solvent 2-5 | 2.9 | 1.04 | 21 | 0.56 | 262 | 0.16 | 99.1 | 0.61 |
| Solvent 2-6 | 2.6 | 1.04 | 23 | 0.57 | 330 | 0.28 | 98.8 | 0.82 |

Analytical data of the solid bottom fractions for Test Runs 2-1, 2-2, 2-5 and 2-6 are shown herein in Table 6 as Solids 2-1, 2-2, 2-5 and 2-6, respectively.

TABLE 6

| | Solid Bottom Fractions | | | | | |
|---|---|---|---|---|---|---|
| Sample | Moisture (wt %) | Furans (wt %) | Sugars (wt %) | Organic acids (wt %) | Dioxane (wt %) | C/H/N/S/O (wt %) | Ash, 700° C. (wt %) |
| Solid 2-1 | 1.15 | — | — | — | — | 58.7/4.7/0.23/0/34.2 | 1.06 |
| Solid 2-2 | 0.50 | 1.61 | 0.17 | 0.18 | 0.18 | 60.6/4.6/0.21/0/32.6 | 1.49 |
| Solid 2-5 | 1.88 | 4.4 | 0.17 | 0.68 | 0.37 | 61.9/4.4/0.16/0/30.1 | 0.99 |
| Solid 2-6 | 0.62 | 1.36 | 0.21 | 0.14 | 0.13 | 61.3/4.6/0.23/0/30.7 | 1.09 |

Example 3

Example 3 describes washing procedures for the reduction of ash content in the bottom fractions.

Solid 3-1: Solid 1-3, describe in Example 1, was stirred in deionized water (20×sample weight) for 16 h at ambient temperature. The solids were filtered off and dried overnight at 105° C. to obtain Solid 3-1.

Solid 3-2: Solid 2-2 (95.7 g), described in Example 2, was stirred in deionized water (300 g) for 19 h in ambient temperature. The solids were filtered off and dried overnight at 105° C. to obtain Solid 3-2 (82 g, 85.7 wt %).

Solid 3-3: Solid 2-5 (96.2 g), described in Example 2, was stirred in deionized water (300 g) for 19 h in ambient temperature. The solids were filtered off and dried overnight at 105° C. and the residue was then stirred in abs. ethanol (240 g) for 26 h in ambient temperature. The solids were filtered off and dried overnight at 105° C. to obtain Solid 3-3 (81.3 g, 84.5 wt %).

Solid 3-4: Solid 2-5, described in Example 2, was stirred in deionized water (4×sample weight) for 6 h at 60° C. The solids were filtered off and dried overnight at 105° C. to obtain Solid 3-4.

Solid 3-5: Solid 2-5, described in Example 2, was stirred in citric acid solution (5 wt % aq., 4×sample weight) for 6 h at 60° C. The solids were filtered off, washed with deionized water and dried overnight at 105° C. to obtain Solid 3-5.

The difference in ash content between washed and unwashed solid samples corresponds to removal of residual NaBr and is shown herein in Table 7.

TABLE 7

| | Washing of solid fractions | | | | | |
|---|---|---|---|---|---|---|
| Sample | C wt % | H wt % | N wt % | S wt % | O wt % | Ash, 700° C. wt % |
| Solid 3-1 | 60.9 | 4.48 | 0.29 | 0.0 | 29.7 | 0.30 |
| Solid 3-2 | 61.4 | 4.5 | 0.21 | 0.0 | 31.9 | 0.48 |
| Solid 3-3 | 63.4 | 4.3 | 0.19 | 0.0 | 29.1 | 0.45 |
| Solid 3-4 | — | — | — | — | — | 0.59 |
| Solid 3-5 | — | — | — | — | — | 0.90 |

Example 4

Example 4 describes a high temperature carbonization of Solid 3-1, described in Example 3, to form Solid 4-1. A fine powder of Solid 3-1 (3.2 g) was heated to a $T_{max}$ of 1000° C. under $N_2$ at a rate of 10 K/min, with a hold time at $T_{max}$ of 1 h. The heat was then removed and the temperature of the material was allowed to cool to room temperature under $N_2$. The residue Solid 4-1, 1.45 g (45.3 wt. % of 1-3) was collected as a fine black powder. Elemental and ash content analysis of Solid 3-1 and 4-1 are shown herein in Table 8.

TABLE 8

High Temperature Carbonization

| Sample | C wt % | H wt % | N wt % | S wt % | O wt % | Ash, 925° C. wt % |
|---|---|---|---|---|---|---|
| Solid 3-1 | 60.9 | 4.48 | 0.29 | 0.0 | 29.7 | 0.28 |
| Solid 4-1 | 98.3 | 0.37 | 0.82 | 0.0 | 0.13 | 0.27 |

Example 5

Example 5 describes the high temperature carbonization of Solid 3-2 to form Solid 5-1 and 5-2. A fine powder of Solid 3-2 (50.5 g), described in Example 3, was heated to a $T_{max}$ of 500° C. under $N_2$ at a rate of 10 K/min, with a hold time at $T_{max}$ of 1 h. The heat was then removed and the temperature of the material was allowed to cool to room temperature under $N_2$. Solid 5-1, 28.2 g (55.8 wt %), was collected as a fine brown/black powder.

Solid 5-1 (25.2 g) was then heated to a $T_{max}$ of 1000° C. under $N_2$ at a rate of 10 K/min, with a hold time at $T_{max}$ of 1 h. The heat was then removed and the temperature of the material was allowed to cool to room temperature under $N_2$. Solid 5-2, 20.2 g (80.2 wt %), was collected as a fine black powder, with an overall yield of 44.8 wt %. Elemental and ash content analysis, and particle size distribution of Solid 3-2, 5-1 and 5-2 are shown herein in Table 9.

TABLE 9

High Temperature Carbonization

| Sample | C wt % | H wt % | N wt % | S wt % | O wt % | Ash wt % * | PSD d10 (µm) | PSD d50 (µm) | PSD d90 (µm) |
|---|---|---|---|---|---|---|---|---|---|
| Solid 3-2 | 61.4 | 4.51 | 0.21 | 0.0 | 31.9 | 0.48 | 14.1 | 40.8 | 86.5 |
| Solid 5-1 | 85.2 | 3.11 | 0.07 | 0.0 | 10.0 | — | — | — | — |
| Solid 5-2 | 95.9 | 0.42 | 0.26 | 0.0 | 1.44 | 0.98 | 15.4 | 40.9 | 99.1 |

* Determined at 925° C. under ambient air flow

Example 6

Example 6 describes the high temperature carbonization of Solid 3-3 to form Solid 6-1 and 6-2. A fine powder of Solid 3-3 (50.3 g), described in Example 3, was heated to a $T_{max}$ of 500° C. under $N_2$ at a rate of 10 K/min, with a hold time at $T_{max}$ of 1 h. The heat was then removed and the temperature of the material was allowed to cool to room temperature under $N_2$. The Solid 6-1, 30.4 g (60.4 wt %), was collected as a fine brown/black powder.

Solid 6-1 (27.6 g) was then heated to a $T_{max}$ of 1000° C. under $N_2$ at a rate of 10 K/min, with a hold time at $T_{max}$ of 1 h. The heat was then removed and the temperature of the material was allowed to cool to reach room temperature under $N_2$. Solid 6-2, 22.1 g (80.1 wt %), was collected as a fine black powder, with an overall yield of 48.4 wt %. Elemental and ash content analysis, and particle size distribution of Solid 3-3, 6-1 and 6-2 are shown herein in Table 10.

TABLE 10

High Temperature Carbonization

| Sample | C wt % | H wt % | N wt % | S wt % | O wt % | Ash, 925° C. wt % |
|---|---|---|---|---|---|---|
| Solid 3-3 | 63.4 | 4.32 | 0.19 | 0.0 | 29.1 | 0.45 |
| Solid 5-1 | 84.5 | 3.19 | 0.08 | 0.0 | 10.6 | — |
| Solid 5-2 | 96.0 | 0.40 | 0.37 | 0.0 | 1.49 | 0.67 |

Example 7

Example 7 describes fractionation distillation of collected solvent distillates. 363.8 g of Solvent 2-6, described in Example 2, was heated to reflux in 1 L round bottom flask equipped with a Vigreux column, distillation head with a thermometer connected to a condenser and a fraction collector. The solvent distillate was distilled and collected in two fractions, Solvent 7-1 and Solvent 7-2. The analytical data is shown herein in Table 11.

TABLE 11

Fractional Solvent Distillates

| Sample | Amount (g) | Head T (° C.) | Density (g/mL) | pH | Dioxane (wt %) | Water (wt %) | Furans (ppm) | Org. acids (wt %) | Dioxane recovery (%) |
|---|---|---|---|---|---|---|---|---|---|
| Solvent 2-6 | 363.8 | — | 1.039 | 2.6 | 67.5 | 31.2 | 5670 | 0.28 | — |
| Solvent 7-1 | 295.5 | 87-88 | 1.036 | 5.4 | 82.1 | 18.0 | 62 | <0.01 | 98.8 |
| Solvent 7-2 | 60.3 | 88-99 | 1.004 | 2.2 | 5.7 | 92.7 | 2150 | 0.97 | 1.4 |

Summary of Examples 1-7

Examples 1-7 demonstrate that a horizontal thin-film evaporator may be effectively used to separate solvents (as a vapor fraction) and organic impurities (as a solid bottom fraction) and allows for solvent recovery and impurity removal from sugar dehydration processes such as fructose dehydration to HMF and xylose dehydration to furfural. These processes demonstrate that when the feed comprises humins, residual sugars, furan-containing organic compounds and organic acids, a high solvent recovery (90-100%) may be achieved based on low residual solvent content in solid bottom fraction. The recovered solvent had low residual organic impurity content, <4 wt % and sometimes <2 wt %. Such recovered solvent with low residual impurities can be further purified (>99%), such as by either vapor-fed continuous distillation or sequential fractionation distillation of condensed distillates.

Recovery and discharge of organic impurities as a dry solid bottom fraction showed <2 wt % residual moisture and a low-ash and sulfur-free solid fraction after water wash. These solid bottom fractions may be further processed and used as an anode material for energy storage applications, activated carbons for purification processes, or can be incorporated into a soil enhancer, amendment, fertilizer or a soil purifier.

While preferred embodiments of the disclosure have been illustrated and described, it will be appreciated that various changes can be made therein without departing from the spirit and scope of the disclosure. Therefore it should be clearly understood that the forms disclosed herein are illustrative only and are not intended to limit the scope of the present disclosure.

What is claimed is:

1. A process for isolating humins from a feed source, comprising:
    providing a feed source to a thin-film evaporator, wherein the feed source comprises:
        a multicomponent solvent comprising water and a water-miscible aprotic organic solvent; and
        a dissolved dry residue comprising a humin compound content;
    wherein the feed source has a pH of between about 1-4 pH; and
    processing the feed source within the thin-film evaporator to provide an isolated solid material comprising:
        a moisture content of about 0.3-2 wt. %;
        a furan containing compound content of about 0.9-5 wt. %;
        a sugar content of about 0.1-2 wt. %;
        a dioxane content of about 0.02-1 wt. %; and
        an ash content of about 0.1-6 wt. %.

2. The process of claim 1,
wherein the feed source comprises:
    about 65-90 wt. % of a multicomponent solvent comprising water and a water-miscible aprotic organic solvent; and
    about 10-35 wt. % of a dissolved dry residue comprising, in wt. % or ppm of the total feed source:
        a sugar content of about 30,000-120,000 ppm;
        a furan containing compound content of about 2-5 wt. %;
        a humin compound content of about 24,000-100,000 ppm;
        an organic acid content of about 0.2-0.7 wt %;
        a homogenous acid;
        a salt; and
        a metal.

3. The process of claim 1, further comprising washing and drying the isolated solid material to produce a washed and dried solid material.

4. The process of claim 3, further comprising exposing the washed and dried solid material to a high temperature carbonization process to produce a carbonized solid material.

5. The process of claim 1, wherein the thin-film evaporator is a horizontal thin film evaporator.

6. The process of claim 1, wherein the thin-film evaporator is orientated at an angle between about 0° to 90°, wherein 0° corresponds to the heated thin film evaporator being oriented straight down, toward the Earth's center of mass and 180° corresponds to the heated thin film evaporator being oriented straight up, away from the Earth's center of mass.

7. The process of claim 2, wherein the organic acid is selected from the group consisting of levulinic acid, formic acid, acetic acid, and combinations thereof.

8. The process of claim 2, wherein the homogenous acid is selected from the group consisting of HCl, HBr, HI, $H_2SO_4$, $H_3PO_4$, oxalic acid, triflic acid, methane sulfonic acid, boron trihalides, and combinations thereof.

9. The process of claim 2, wherein the salt is selected from the group consisting of sodium bromide, calcium bromide, sodium chloride, calcium chloride, potassium chloride, potassium chloride, magnesium chloride, magnesium chloride, and combinations thereof.

* * * * *